US005506255A

United States Patent [19]

Smith et al.

[11] Patent Number: 5,506,255
[45] Date of Patent: Apr. 9, 1996

[54] RHODOPORPHYRIN AND PHYLLOERYTHRIN RELATED PHOTOSENSITIZERS FOR PHOTODYNAMIC THERAPY

[75] Inventors: Kevin M. Smith, Davis, Calif.; Ravindra K. Pandey, Williamsville, N.Y.; Joseph M. Ryan, Sacramento, Calif.; Nadine Jagerovic, Savigny les Beaune, France; Thomas J. Dougherty, Grand Island, N.Y.

[73] Assignee: The Regents of the University of California, Oakland, Calif.

[21] Appl. No.: 160,384

[22] Filed: Dec. 1, 1993

Related U.S. Application Data

[63] Continuation-in-part of Ser. No. 840,347, Feb. 24, 1992, Pat. No. 5,330,741.

[51] Int. Cl.⁶ .................. A61K 31/40; C07D 487/22
[52] U.S. Cl. ............................. 514/410; 540/145
[58] Field of Search ..................... 540/145; 514/410

[56] References Cited

U.S. PATENT DOCUMENTS

| | | | |
|---|---|---|---|
| 4,920,143 | 4/1990 | Levy et al. | 514/410 |
| 5,087,636 | 2/1992 | Jamieson et al. | 514/410 |
| 5,095,030 | 3/1992 | Levy et al. | 514/410 |
| 5,171,749 | 12/1992 | Levy et al. | 514/410 |
| 5,238,940 | 8/1993 | Liu et al. | 514/410 |
| 5,283,255 | 2/1994 | Levy et al. | 514/410 |
| 5,354,858 | 10/1994 | Morgan et al. | 540/145 |

OTHER PUBLICATIONS

Pandey et al, Chemical Abstracts, vol. 121 (1993) 108319.
Smith, Kevin, M., et al., "Meso Substitution of Chlorophyll Derivatives: Direct Route for Transformation of Bacteriopheophorbides d into Bacteriopheophorbides c", *The American Chemical Society*, 107, 4946–4954, (1985).
Meunier, Isabelle, et al., "New Syntheses of Benzoporphyrin Derivatives and Analogues for Use in Photodynamic Therapy", *Bioorganic & Medical Chemistry Letters*, vol. 2, No. 22, pp. 1575–1580, (1992).
Pandey, Ravindra, K., et al., "Efficient Synthesis of new Classes of Regiochemically Pure Benzoporphyrin Derivatives", *Bioorganic & Medicinal Chemistry Letters*, vol. 3, No. 12, pp. 2615–2618, (1993).
Meunier, Isabelle, et al., "Benzoporphyrin Derivatives: Synthesis, Structure and Preliminary Biological Activity", *J. Chem. Soc. Perkin Trans.*, pp. 961–969, (1994).
Callott, Henry, J., et al., "Additions to Porphins involving the Formation of New Carbon–Carbon Bonds", *J. Chem. Soc. Perkin Trans. I*, 1424 (1973).

*Primary Examiner*—Richard L. Raymond
*Attorney, Agent, or Firm*—Hana Verny

[57] ABSTRACT

Novel photosensitizers related to rhodoporphyrins and phylloerythrin methyl ester, their preparation and use as photosensitizers for detection and treatment of tumors by photodynamic therapy. The novel photosensitizers accumulate and concentrate preferentially in tumor tissue, have strong light absorption in the 650 to 700 nm region and have reduced skin phototoxicity.

7 Claims, No Drawings

RHODOPORPHYRIN AND PHYLLOERYTHRIN RELATED PHOTOSENSITIZERS FOR PHOTODYNAMIC THERAPY

This invention was made in the course of research supported by the research Grant No. HL-22252 awarded by the National Institute of Health. The United States Government has certain rights in this invention.

This invention is a continuation-in-part of the U.S. application Ser. No. 07/840,347 filed Feb. 24, 1992, now U.S. Pat. No. 5,330,741.

BACKGROUND OF THE INVENTION

1. Field of Invention

This invention concerns novel photosensitizers related to rhodoporphyrins and phylloerythrin methyl ester useful for photodynamic therapy. In particular, this invention concerns a variety of rhodoporphyrins, rhodochlorins, mesorhodochlorins, phylloerythrin derivatives, and their preparation and use as photosensitizers for detection and treatment of tumors by photodynamic therapy. The novel photosensitizers accumulate and concentrate preferentially in tumor tissue, have strong light absorption in the 650 to 900 nm region and have reduced skin phototoxicity.

2. Background and Related Art

In the last decade, a photodynamic therapy (PDT) appeared as a new and viable approach to cancer diagnosis and therapy. Photodynamic therapy involves systemic administration of a photosensitizer, a photosensitive compound which in itself is essentially therapeutically inactive but which accumulates preferentially in tumor tissue and absorbs light at wavelength between 660 and 880 mm. The administration of the photosensitizer is followed by illumination with visible light. The lesion or tumor is detected by a presence of the accumulated photosensitizer with visible light. The treatment of tumors by photodynamic therapy, therefore, requires photosensitizers which accumulate in tumor tissue, which are distinguished by large quantum yield to sensitize the formation of singlet oxygen, and which have strong absorption in the spectral region where tissue transmits best, that is between 660 to 800 nm.

Photodynamic therapy (PDT) has been first described in *Cancer Res.*, 38:2628 (1976) and since then it has been used experimentally in cancer patients with an estimated 3,000–4,000 patients treated world-wide. PDT is based on findings published in *J. Natl. Cancer Inst.*, 26:1 (1961) that a derivatized hematoporphyrin (HpD) which has fluorescent properties is selectively uptaken by malignant tissue. Subsequently, studies described in *Ann. Surg.*, 167:829 (1968) indicated that photphyrin hematoporphyrin derivative (HpD) is taken up by a wide variety of carcinomas and sarcomas both in man and animals. The actual therapeutic potential of HpD for treatment of a metastatic breast cancer with light was first disclosed in *Proc. IX Int. Cancer Congress*, 393 (1966) which describes a positive tumor response to this treatment.

In 1975, *J. Natl. Cancer Inst.*, 55:115 (1975) reported that a transplanted mammary tumor in mice could be eradicated completely using filtered red light following systemic injection of HpD and about the same time, a positive tumor response to a treatment of a bladder tumor was described in a patient injected with HpD by delivering light endoscopically via a glass light guide. In response to the treatment, the tumor size decreased in the treated area with no apparent effect in the untreated area. These findings were reported in *J. Urol.*, 155:150 (1976). Since that time, numerous clinical trials using HpD have been reported encompassing essentially all solid tumors accessible on the skin surface or endoscopically.

So far, several groups of compounds are known to act as photosensitizers. HpD, available as Photofrin I and its more purified version Photofrin II are the first clinically approved photosensitizers developed by Quadra Logic Technologies and Lederle Laboratories. They are prepared by acid catalyzed acetylation of hematoporphyrin (Hp) and subsequent alkaline treatment. These compounds are complex oligomeric mixtures contaminated with starting hematoporphyrin and its dehydration products. The oligomeric mixtures which comprise 50 to 80% of the tumor-localizing fraction of HpD are selectively retained in the tumors and are responsible for both the in vivo fluorescence and for photosensitizing properties of HpD.

In spite of the potential broad diagnostic and therapeutic application of PDT in clinical oncology, there are disadvantages connected with use of HpD because of the lack of a complete understanding of which active component or components in the HpD complex are responsible for tumor uptake and retention. Moreover, the limited tumor selectivity of HpD, the limited tissue penetration of the light upon treatment following HpD administration by systemic injection and limited retention by malignant tissues were observed.

Photodynamic treatment with porphyrins is further complicated by observation that normal nontumorous organs such as liver, kidney, spleen and skin tend to retain considerable amounts of the porphyrins. The porphyrins accumulated in these nontumorigenic tissues react, upon light illumination, exactly as the porphyrins in the tumor tissue, that is by producing cytotoxic singlet oxygen which assert a cytotoxic activity on the normal tissue, thereby causing severe tissue damage and other undesirable side effects. Another problem associated with this treatment is a skin photosensitivity. In order to avoid cutaneous phototoxicity following the treatment with a photosensitizer, a patient must remain in subdued light for four to six weeks after HpD administration.

The other major drawback of HpD is its weak absorbance at 630 nm, the wavelength of red light most commonly used in PDT. Incomplete responses to the HpD treatment in some cases were attributed to the difficulty in delivering light to some tumor sites and to incomplete light penetration for larger tumors due to its weak absorbance.

These problems have resulted in considerable efforts devoted to developing new photosensitizers having increased absorption maxima in the 600–800 nm region in order to increase the efficiency of the light as well as to achieve greater tissue penetration with the longer wavelengths.

Several new classes of photosensitizers for use in PDT are derived from tetrapyroles and their derivatives. Tetrapyrolic macrocycles are the most ubiquitous of all naturally occurring pigments and most of them generate high quantum yields of triplet states from which energy transfer to ground state oxygen appears to be the most dominant process. Synthetic etiopurpurin, benzochlorines, rhodins, verdins, and methyl pyrroverdin as well as the novel pentapyrolic macrocycles pentaphyrin and sapphyrin have shown very promising results in PDT, and are considered to be a new generation of PDT photosensitizers. While these compounds seem to possess absorption wavelength maxima around 750–800 nm, some of these compounds are highly unstable and thus not overly suitable and practical for diagnostic and therapeutic purposes.

Tetrapyrrole compounds and a process for the production of thereof useful in photodiagnosis and phototherapy is described in the EPO patent application 85108981.3 filed on Jul. 18, 1985.

Phthalocyanines and their derivatives are another class of new photosensitizers under investigation. They are structurally related to the naturally occurring porphyrins but have the four isoindole units linked by aza-nitrogens rather than methane linkages. These compounds show strong absorption in the 650–700 nm range, and certain non-metallo as well as metallo derivatives exhibit efficient photochemical processes. However, since the most studied sulfonated phthalocyanines are composed of mono-, di-, tri- and tetrasulfonated species, they may not be the most suitable for human use.

So far the most promising new second generation photosensitizer closest to the clinic is mono-L-aspartylchlorin $E_6$ (MACE) and a related compound di-L-aspartyl-chlorin-$e_6$ (DACE) which possess strong absorption bands with high molar extinction coefficients around 664 nm. MACE and DACE are prepared by alkaline degradation from methyl pheophorbide-a followed by esterification with diazomethane to give chlorin $E_6$ trimethyl ester, which is then converted to the acid chloride. Aspartic acid is then added using usual peptide chemistry.

Initial PDT experiments demonstrated that MACE was ineffective at inducing tumor cures when a 24 hours time interval between drug administration and light treatment was used. However, when MACE was administered 4–6 hours prior to light exposure, PDT induced tumor cures were obtained. In addition, at comparable drug and light doses, the level of PDT induced normal skin damage was significantly lesser for MACE than for HpD. The results of testing indicated that MACE is a short-acting but not overly effective tumor photosensitizer with good in vivo clearance properties. The characterization of MACE and DACE is described in *J. Natl. Cancer Inst.*, 80:330 (1988).

Purpurin-18 and chlorin-$p_6$, two derivatives of chlorophyll, described in *Photochemistry and Photobiology*, 48:579 (1988) were found to be potent photosensitizers which promote cell killing by low intensity of red light Recently, a new class of compounds, namely chlorophyll-a derivatives were found to be very potent photosensitizers. These compounds are disclosed in the copending patent application Ser. No. 07/840,347 filed on Feb. 24, 1992, now U.S. Pat. No. 5,330,741, which is hereby incorporated by reference in its entirety.

The porphyrin and chlorin derivatives which have led to the development of the current invention have been reviewed in Proc. SPIT, 1065:164 (1989). The aspartyl derivatives of chlorin $E_6$, monoaspartyl chlorin $E_6$, and diaspartyl chlorin $E_6$ were found to be effective photosensitizers in vitro. With these compounds, the aspartyl group was noted to be responsible for the efficiency of tissue clearance. In pheophorbide and pyropheophorbide and chlorin $E_6$ series, certain alkyl ether derivatives, including 2-(1-hexyloxyethyl)2-des vinyl derivatives, were found to be excellent photosensitizers compared with their parent compounds, methyl pyropheophorbide-a, pyropheophorbide-a and chlorine $E_6$. Chlorin-$e_6$ esters were found to be slightly less effective than methyl pheophorbide-a and pyrophorbide-a analogs, indicating that either the E-ring is an important factor in photoactivity or that due to its increase in hydrophility, E-ring is not retained in the tumor cells for longer time than the n-hexyl or n-heptyl ether derivatives of pyropheophorbide-a. Among recently newly discovered photosensitizers, some benzoporphyrin derivatives (BPD), usually as a mixture of isomers, have also been reported in *J. Natl. Cancer Inst.*, 79:1327 (1987).

In recent years there has been increased interest in synthesis of long wavelength photosensitizers for use in photodynamic therapy which would result in deeper tissue penetration and allow treatment of larger tumors, particularly, if these new photosensitizers would have reduced skin phototoxicity.

Some attempts to provide such photosensitizers were recently described. However, these attempts were only partially successful. The synthesis of benzoporphyrin derivatives (BPD) from protoporphyrin IX dimethylester according to method described in *J. Natl. Cancer Inst.*, 79:1327 (1987) lacks regiochemical control resulting in a mixture of active and inactive compounds requiring extensive purification before biological studies of these compounds could be done. These compounds showed good vitro photosensitizing efficacy. However, in vivo these compounds were effective only when the animals were treated 3 hours post i.v. injection of the drug. When the treatment was done 24 hours post injection of the drug, even at higher doses (5 mg/kg), no tumor response was observed. These compounds therefore seem to have little tumor selectivity.

A recent methodological advancement described in *Bioorg. Med. Chem. Letr.*, 2:1575 (1992) reduces the separation problems observed above. The method uses 4-acetyl-2-vinyldeuteroporphyrin IX dimethyl ester as a starting material. Since only one vinyl group is present, the additional purification step after Diels-Alder coupling is unnecessary. Although this method has advantages over using the divinylporphyrin, it still requires the synthesis and separation of the two hydroxyethyl isomers obtained from partial reduction of diacetyldeuteroporphyrin IX dimethyl ester.

This invention, consequently, provides a variety of benzoporphyrin derivatives derived from rhodoporphyrins and phylloerythrin methyl ester related photosensitizers. These new photosensitizers are stable compounds which are easy to synthesize, which are able to penetrate deeper in the tissue and therefore allow treatment of larger tumors. The new photosensitizers have substantially reduced skin phototoxicity compared to Photofrine.

All patents, patent applications and publications cited herein are hereby incorporated by reference in their entirety.

SUMMARY

One aspect of the current invention are novel photosensitizers which are related to benzoporphyrins and which are derivatives of rhodoporphyrins and phylloerythrin methyl ester.

Another aspect of the current invention are photosensitizers derived from rhodorphin IX dimethylester.

Still another aspect of the current invention are photosensitizers derived from ketal or thioketal analogues of phylloerythrin methyl ester.

Yet another aspect of the current invention are photosensitizers having a vinyl group at position 2 which allows production of ring A chlorin after the Diels-Alder reaction.

Another aspect of the current invention is a compound of the formula

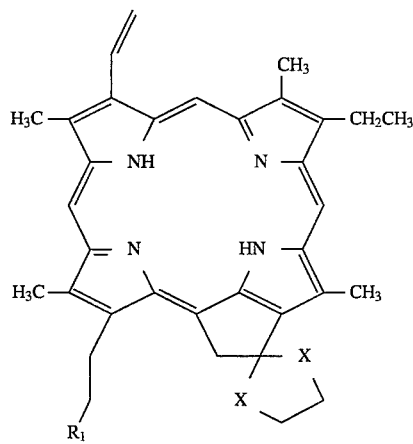

wherein $R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and wherein X is oxygen or sulphur;

and the pharmaceutically acceptable salts and esters thereof.

Another aspect of the current invention is a compound of the formula

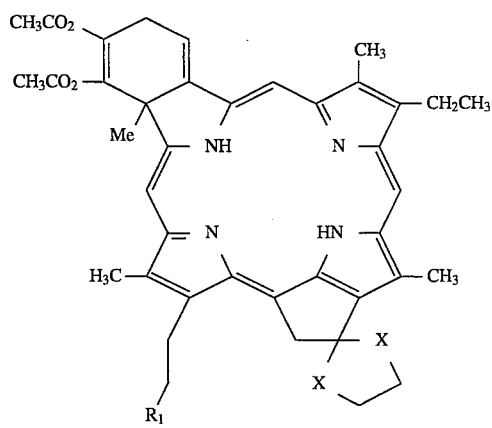

wherein $R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and wherein X is oxygen or sulphur;

and the pharmaceutically acceptable salts and esters thereof.

Another aspect of the current invention is a compound of the formula

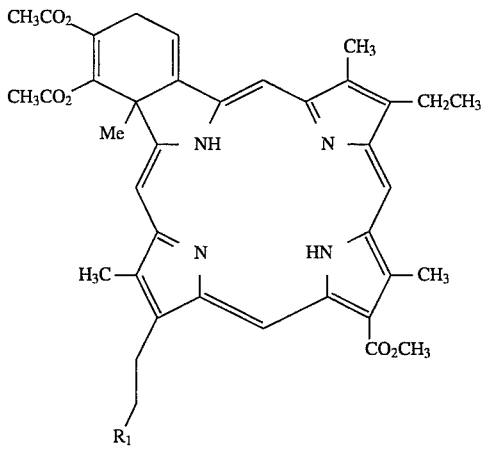

wherein $R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and wherein X is oxygen or sulphur;

and the pharmaceutically acceptable salts and esters thereof.

Another aspect of the current invention is a compound of the formula

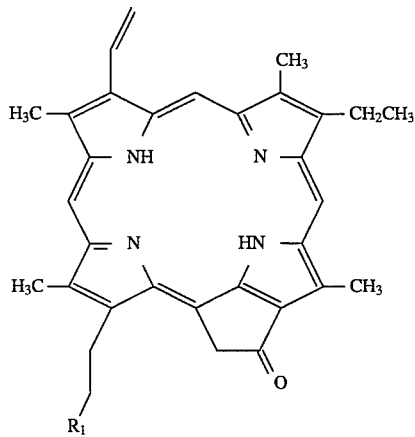

wherein $R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and wherein X is oxygen or sulphur;

and the pharmaceutically acceptable salts and esters thereof.

Another aspect of the current invention is a A compound of the formula

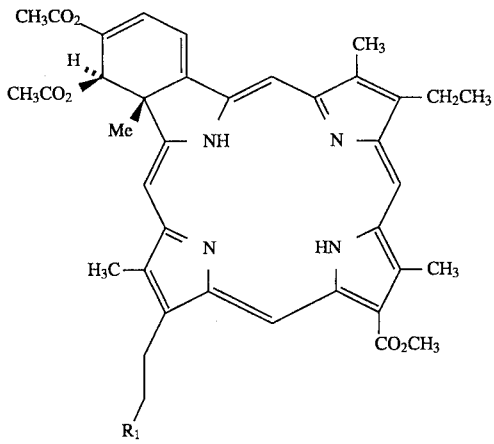

wherein
$R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and
wherein X is oxygen or sulphur;
and the pharmaceutically acceptable salts and esters thereof.

Another aspect of the current invention is a compound of the formula

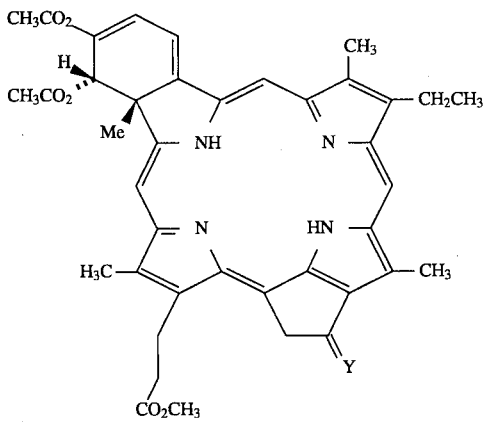

wherein
$R_1$ is $COOR_2$ wherein $R_2$ is H or lower alkyl having from 1–4 carbon atoms, or —$CONHCH(COOR_3)CH_2(COOR_3)$; wherein is $R_3$ is H or lower alkyl having 1–4 carbon atoms; and
wherein Y is O, —$OCH_2CH_2O$—; or —$SCH_2CH_2S$—;
and the pharmaceutically acceptable salts and esters thereof.

Still yet another aspect of the current invention is a method for diagnosis and therapy of tumors and cancerogenic growths by administering to a patient a sufficient amount of a photosensitizer of the current invention and subsequently exposing the patient to a light of appropriate wavelength which achieves a maximal photosensitization.

DEFINITIONS

As used herein

"Diels-Alder adduct" means a product of 1,4 addition of a conjugated diolefin to a dienophile compound containing a double or triple bond. Dienophile may be activated by conjugation with a second double bond or with an electron acceptor.

"DDQ" means 2,3-dichloro-5,6-dicyanobenzoquinone.

DETAILED DESCRIPTION OF THE INVENTION

Current invention concerns novel type of photosensitizers related to benzoporphyrin derivatives which are derived from rhodoporphyrinmethyl ester and from ketal or thioketal analogues of phylloerythrin methyl esters. These photosensitizers include but are not limited to rhodochlorins, rhodoporphyrins, mesorhodochlorins, phylloerythrins, and their derivatives. Preferred photosensitizers are benzoporphyrin derivatives and their respective Diels-Alder adducts and vinyl phylloerythrins derivatives and their respective Diels-Alder adducts. These derivatives possess long wavelength absorption maxima between 600 and 800 nm, are stable, water soluble fast acting.

These novel compounds are selectively taken up by a variety of tumors and their absorption spectra maxima allow the irradiation of these tumors with the red light within the absorption spectra limits without affecting the other tissue. The light irradiation provokes an oxidation process sensitized by the photosensitizer producing cytotoxic singlet oxygen which effectively destroys tumorous cells. These features are extremely important for photodynamic diagnosis and therapy of tumors treated with novel photosensitizers of this invention. Fluorescence spectroscopy also allows diagnosis of tumors.

In order to compare the structure activity relationships among chlorins, pheophorbides and BPDs, a series of novel BPDs as seen in Reaction Schemes 1–7 were prepared. Thus, this invention deals preferably with two series of photosensitizers related to BPDs. On series concerns compounds related and derived from rhodoporphyrin IX dimethylester. The second series concerns compounds related to and derived from phylloerythrin methyl ester.

These two series of compounds were synthesized by using rhodoporphyrin IX dimethylester (8) and ketal or thioketal analogues of phylloerythrin methyl ester (11) and (12) as starting materials. These are ideal substrates to probe structure/activity relationships in the BPD series because both systems have a vinyl group at position 2, i.e., ring A, and thus will produce only ring A chlorin after the Diels-Alder reaction. Also these compounds have only one propionic ester side chain, which can be hydrolyzed to corresponding monocarboxylic acid at the final step of the synthesis. In some of the photosensitizers (28)-(33) the aspartic acid derivatives have shown better photosensitizing efficacy than corresponding methyl ester or as free carboxylic acid derivatives.

Synthesis of Rhodoporphyrin Series Derivatives

Preparation of various rhodorphin derivatives is illustrated generally in Reaction Schemes 1–2. Starting material for rhodorphin series of compound is rhodorphin XV dimethyl ester.

Synthesis of rhodoporphyrin XV dimethyl ester (8) is illustrated in Reaction Scheme 1.

REACTION SCHEME 1

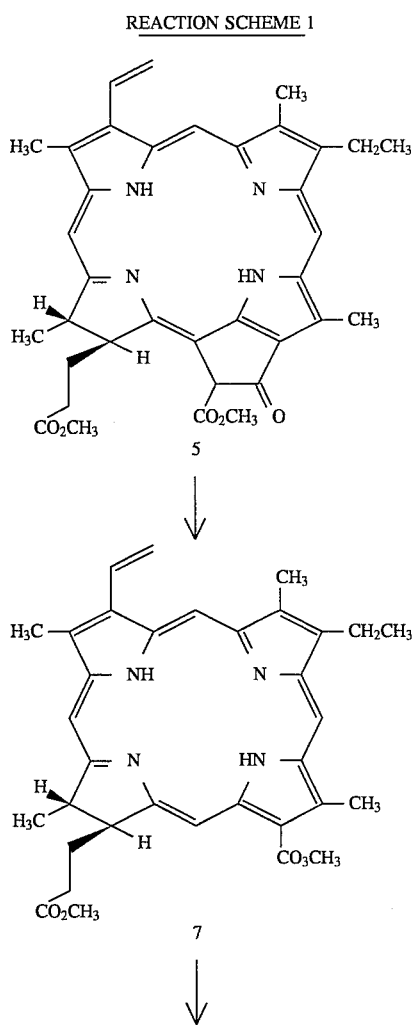

-continued
REACTION SCHEME 1

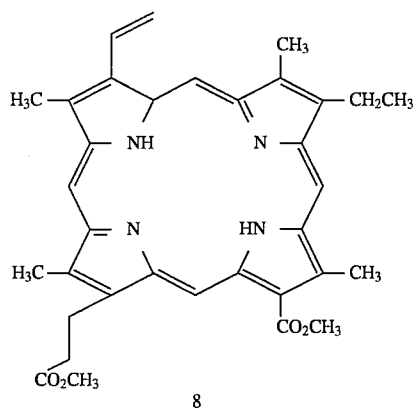

For the synthesis of rhodoporphyrin XV dimethyl ester (8), rhodochlorin XV dimethyl ester (7) is prepared from methyl pheophorbide-a (5) by following the procedure disclosed in G. W. Kenner, S. W. McCombie and K. Smith, *J. Chem. Soc. Parkin, Trans.*, 1:2517 (1973).

Typically, methyl pheophorbide (5) is isolated from spirulina algae, which on aerial oxydation is in alkaline solution, and then refluxed with collidine gives 2-vinyl rhodoporhrin to afford rhodochlorin XV dimethyl ester (7). Rhodochlorin dimethyl ester (7) is dissolved in an organic solvent, preferably in polychlorinated hydrocarbon solvent such as dichloromethane in the presence of 2,3-dichloro-5,6-dicyano-1,4-benzoquinone (DDQ) dissolved in an organic solvent, such as preferably benzene under stirring for about 1–60 minutes. The mixture was passed through alumina column for purification and eluates were collected, organic layer was washed, dried, and purified to afford rhodoporphyrin XV dimethyl ester (8) in 70% yield which was used to prepare cis and trans isomers of benzoporphyrins (15) and (16).

Synthesis of benzoporphyrins (15) and (16) is illustrated in Reaction Scheme 2.

REACTION SCHEME 2

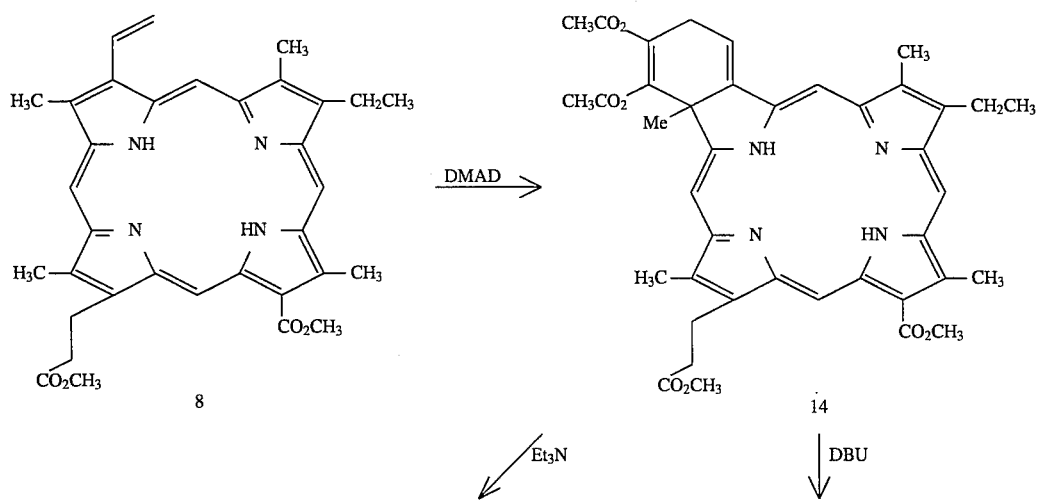

-continued
REACTION SCHEME 2

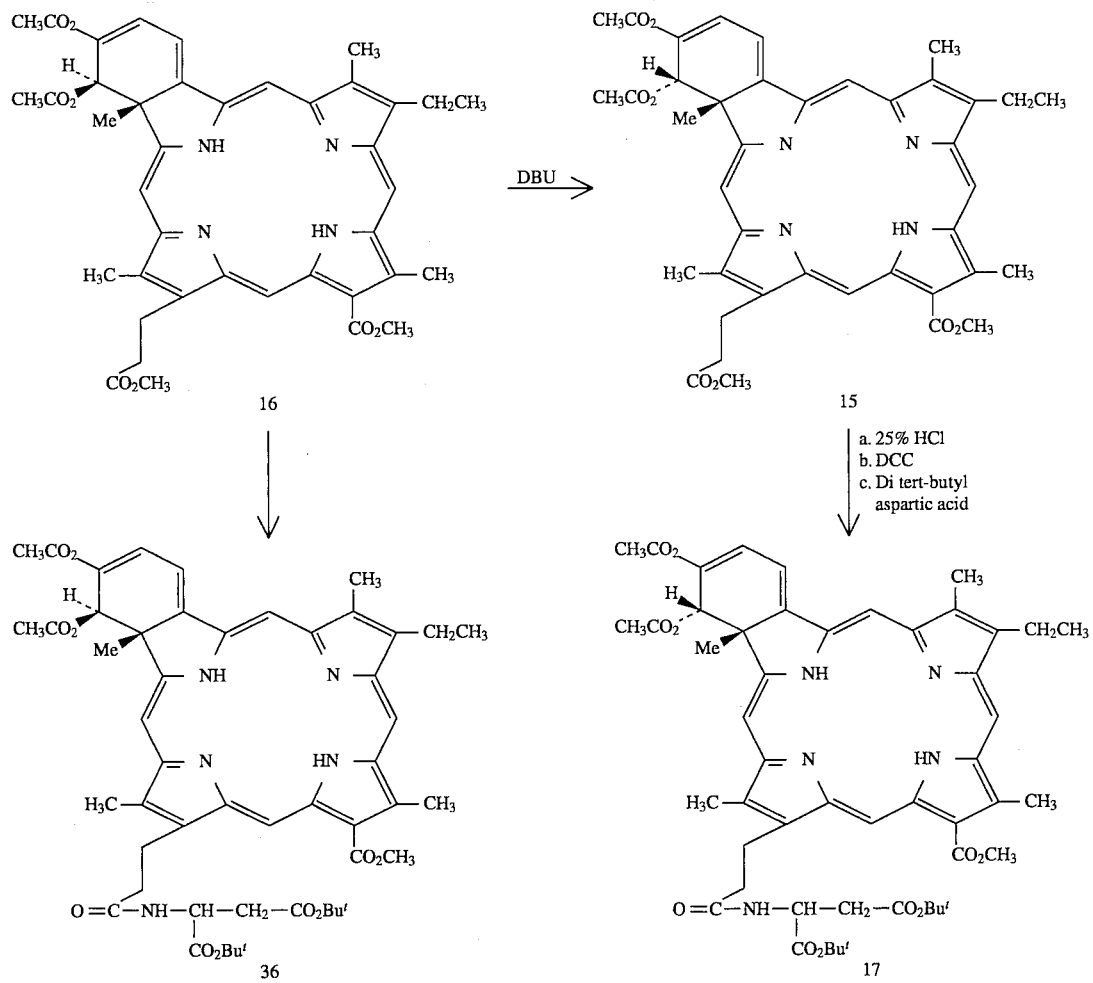

Compound (8) is dissolved in a mixture of a dicarboxylic acid ester, such as dimethylacetylene decarboxylate and an organic solvent such as benzene, under the inert atmosphere, such as under nitrogen, for 30–120, preferably 60 hours.

The solvents are then removed under vacuum and the residue is purified to afford intermediate Diels Alder adduct compound (14). Compound (14) is dissolved in chlorinated hydrocarbon solvent, such as chloroform or preferably in dichloromethane and an amine, such as triethylamine, is added. The reaction is stirred for 1–10, preferably 3 hours, and the solution is evaporated to dryness to afford trans benzoporphyrin isomer (16).

The cis benzoporphyrin isomer (15) is prepared for the intermediate (14) by dissolving it in dichloromethane in the presence of diazobicycloundecane (DBU). The reaction is stirred for a short period of time, preferably around 10 minutes. The resulting solution is purified by chromatography, eluted with preferably dichloromethane and the benzoporphyrin dimethyl ester cis isomer (15) is crystallized.

Benzoporphyrin dimethyl ester (15) is dissolved in an ether, such as tetrahydrofuran acidified with HCl. The mixture is stirred for 6–24 hours, preferably overnight, solvent is evaporated and the residue is purified on a column eluted with a mixture of an alcohol such as methanol, with dichloromethane to afford intermediate carboxylic acid which is, upon evaporation from the solvent, again dissolved in an organic solvent, such as dichloromethane and dicyclohexylcarbodiimide (DCC), dimethylaminopyridine (DMAP) and di-tert-butyl ester of aspartic acid is added. The mixture is stirred for 6–24 hours, preferably overnight at preferably room temperature under inert atmosphere. Solution is then diluted with about 100 ml of dichloromethane and washed, typically with water one or more times. The organic layer is separated, dried and evaporated to give a residue which upon purification provided photosynthesizer compound (17).

Using the same procedure as described above for conversion of compound (15) to cis isomer compound (17), the trans isomer compound (16) is converted to the trans isomer compound (36).

Synthesis of Phylloerythrin Derivatives

Synthesis of phylloerythrin derivatives is illustrated in Reaction Schemes 3–6.

In alternative, reaction of rhodoporphyrin XV dimethyl ester (8) with DMAD, followed by rearrangement of the intermediate (14) with triethylamine, gives the trans-BPD (16), which has a long wavelength maximum at 662 nm. Further treatment of the trans isomer (16) with DBU produces the cis isomer (15), for which the long wavelength absorbance maximum shifted to 668 nm. The overall yield of the desired isomer is about 40%. The cis isomer (15)

obtained directly from the Diels-Alder adduct (14), as described above by rearrangement with DBU, gives lower yields than direct trans to cis conversion.
The synthesis of 2-vinylphylloerythrin methyl ester (13) from methyl pheophorbide-a (6) was accomplished in a fashion shown in Reaction Scheme 3.
REACTION SCHEME 3
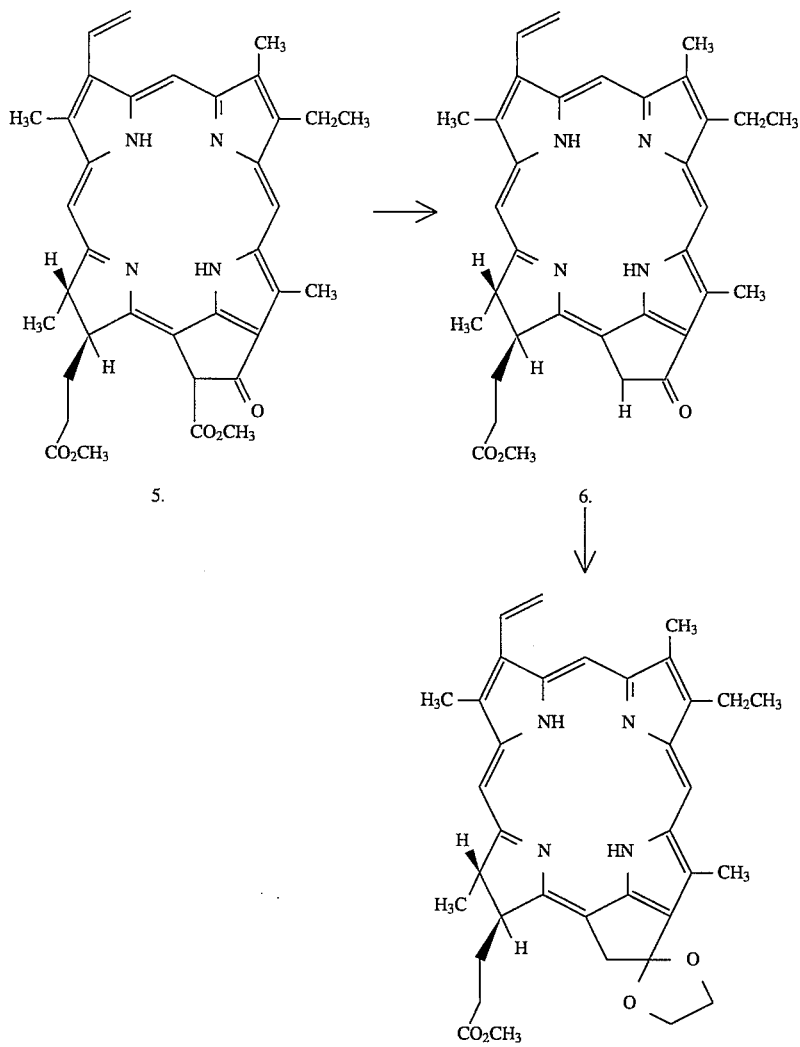

-continued
REACTION SCHEME 3

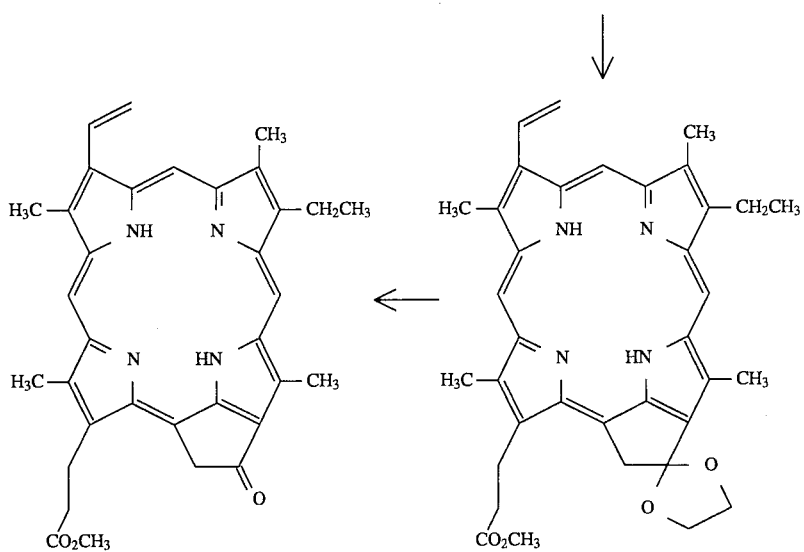

In brief, methyl pheophorbide-a (5) was pyrolysed to methyl pyropheophorbide-a (6) in >95% yield by refluxing in collidine for 90 minutes followed by recrystallization according to K. Smith—Laboratory Methods in Porhyrins and Metalloporphyrins, Elsevier Scientific Publishers, Amsterodam, 777 (1975).

Methyl phlophorbate (6) dissolved in chlorinated hydrocarbon, such as chloroform or carbon tetrachloride, preferably in dry methylene chloride, is stirred under inert atmosphere and an ester, preferably ethylene glycol and trimethylsilyl chloride are added. The mixture is stirred for 6–24, preferably for 12 hours. The reaction is cooled to about −10° C. to −35° C., preferably to about −27° C. and poured into a strong base solution, preferably to about 1N sodium hydroxide. The mixture is partitioned, methylene chloride phase is washed, dried, filtered and evaporated to dryness. After purification, compound (9) is obtained as bright green crystals.

The oxidation of the 9-glycolketal of methyl pyropheophorbide-a (9) with DDQ is required for the preparation of 9-glycoketal-2-vinylphylloerythrin. After recrystallization from the mixture of methylene chloride/methanol, the ketal (9) was found to be stable for an extended time at room temperature in an air tight container. The transformation of the 9-glycolketal of methyl pyropheophorbide-a (9) to the 9-glycolketal of 2-vinylphylloerythrin methyl ester (11) is accomplished in high yield with the addition of about 1.1 equivalence of DDQ in an organic solvent such as benzene at about 0° C. Lastly, the ketal functionality is easily cleaved by stirring with acidic aqueous acetone to give 2-vinylphylloerythrin methyl ester (13).

Compound (11) is dissolved in an ether, such as tetrahydrofurane and an organic solvent, such as preferably acetone is added. The mixture is acidified, methylene chloride is added under stirring and the compound (13) 9 -glycoketal-2-vinylphylloerythrin methyl ester is recrystallized.

The reaction is monitored by UV spectroscopy. 2 -Vinylphylloerythrin methyl ester (13) is a starting compound for preparation of 2-vinylphylloerythrin (33), 2 -vinyl-phylloerythrin di-tert-butylaspartate (34), 9 -glycolketal-2-vinylphylloerythrin-7-detertbutylaspartate (27) and benzoporphyrin derivative cis isomer (31). Preparation of these compounds is illustrated in Reaction Scheme 4.

REACTION SCHEME 4
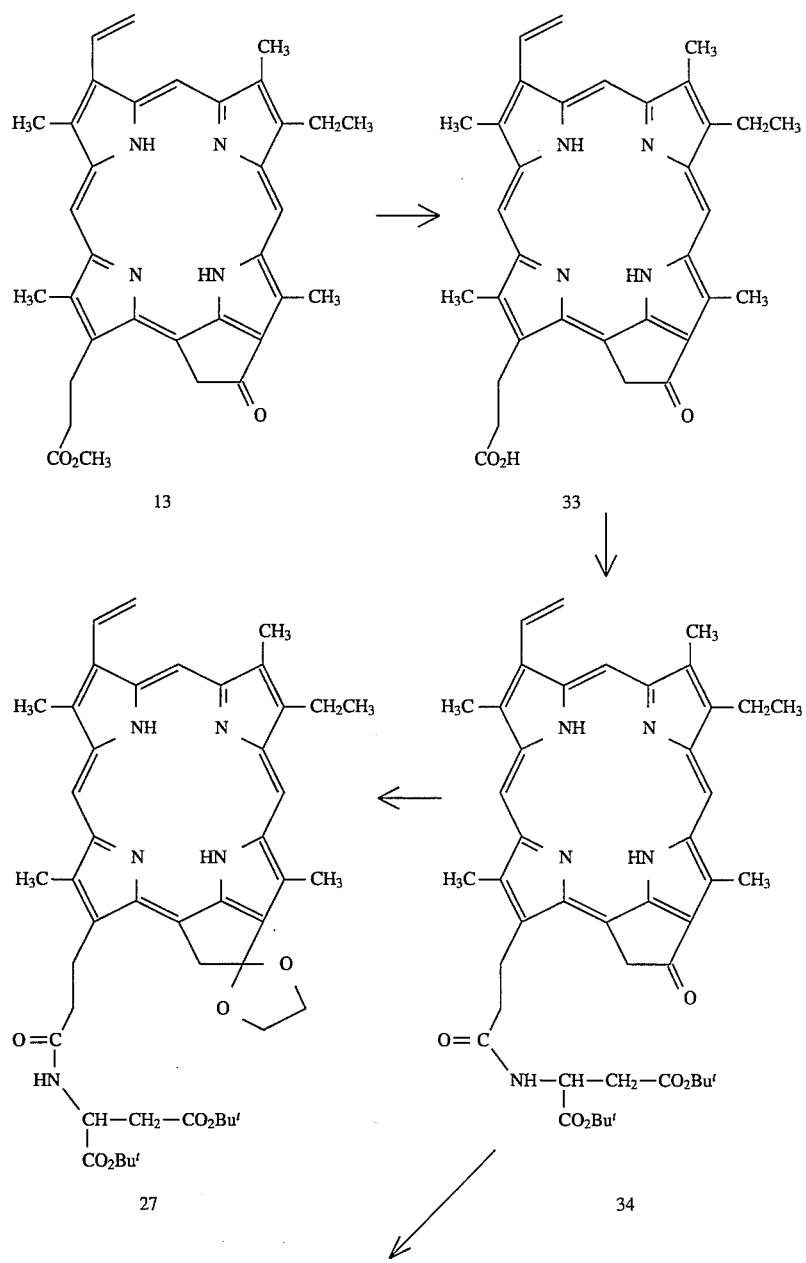

-continued
REACTION SCHEME 4

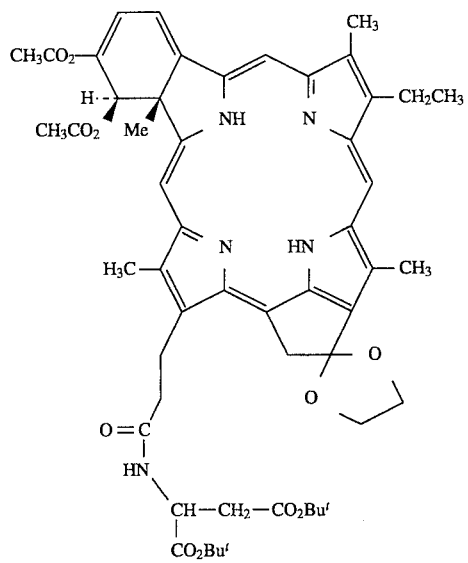

29.

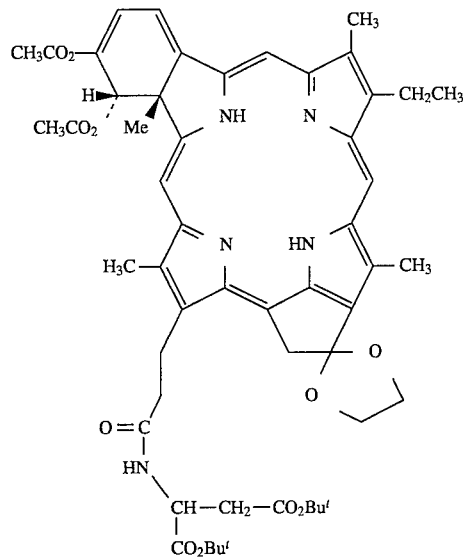

31

The compound (13) is hydrolyzed with an ether, such as furan or preferably tetrahydrofuran, in the presence of a strong base, preferably 1M potassium hydroxide. The mixture is neutralized and cooled to result in a precipitate which, after purification, provides 2-vinylphylloerythrin (33) used for preparation of compound (34) by following essentially the same process as that described for conversion of compound (13) to compound (33). The compound (33) is first hydrolyzed and then converted to the aspartyl amide derivative (34) following methodology described in *J. Natl. Cancer Inst.*, 80:330 (1988).

Compound (34) is converted to a photosensitizer 9-glycolketal-2-vinylphylloerythrin-7-dietertbutylaspartate (27) by treatment with a mixture of solvents, preferably comprising methylene chloride, ethylene glycol and chlorotrimethylsilane. The mixture is stirred under an inert atmosphere for 1–10 hours, preferably for 2 hours. After the purification and the product compound (27) is recrystallized as a red dust.

In alternative, compound (34) can be converted to cis or trans isomer of benzoporphyrin compound (31). Compound (34) is dissolved in an organic solvent, preferably toluene and reacted with dimethylacetylenedicarboxylate (DMAD). The reaction mixture is refluxed for 3–10 days, preferably for about 5 days to obtain Diels-Alder adduct. The reaction is monitored by visible spectroscopy. The reflux Diels-Alder product is purified by dissolving it in a mixture of an amine and polychlorinated hydrocarbon solvents, preferably in a mixture of triethylamine and dichloromethane. The reaction mixture is stirred for about 1–10 hours, preferably for 3 hours, to provide either cis or trans isomer of the resulting compound (31). The formation of appropriate isomer is confirmed by X-rays crystallography.

Diels-Alder adduct of 2-vinylphylloerythrin methyl ester (24) in either cis or trans isomer form is prepared according to Reaction Scheme 5.

REACTION SCHEME 5

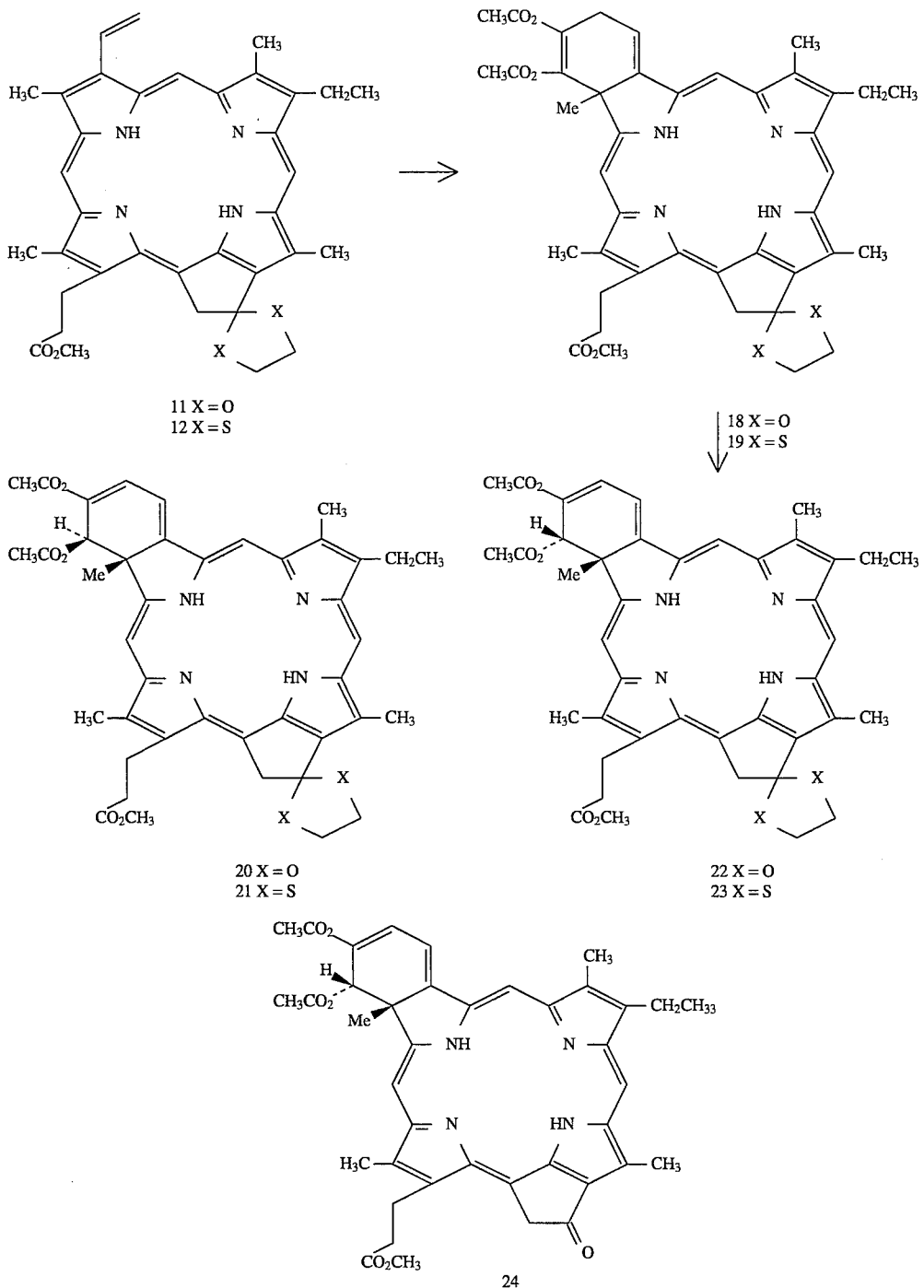

9-glycoketal-2-vinylphylloerythrin methyl ester (11), prepared from 9-glycol ketal-methyl-pyropheophorbide-a (9) is dissolved in an organic solvent, preferably in methylene chloride at low temperature, preferably at about 0° C. and DDQ is slowly added under stirring. After about 3–10 minutes of stirring, the mixture is filtered through alumina. Purification by methods known in the art affords compound (11). Compound (11) is converted to compound (18) by addition of DMAD and dissolving both in an organic solvent, such as benzene or preferably toluene. The reaction mixture is refluxed for 3–10 days, preferably for 5 days, and the reaction is monitored by visible spectroscopy. The purification is achieved by methods described above for compound (31).

Compound (18) is dissolved in an organic solvent, preferably methylene chloride and diazabicycloundecane is added. The reaction mixture is left to react under an inert atmosphere for about 5–30 minutes, preferably for 10 minutes under stirring, and purified as described before for compound (15), yielding compound (22) as cis isomer. For such rearrangement, compound (22) is converted to its Diels-Alder adduct 2-vinylphylloerythrin methyl ester (cis isomer) compound (24) by rearranging compound (22). Compound (22) is typically mixed with an organic solvent, such as acetone and the mixture is acidified. The mixture is stirred for about 3–10, preferably 5 minutes, organic layer is washed, dried and recrystallized to afford cisisomer (24).

Trans isomer is prepared in the same manner except that the Diels-Alder adduct was treated with triethylamine.

Preparation of 9-thioketal-2-vinylphylloerythrin di-tert-butylaspartate derivative (28) and its Diels-Alder products is illustrated in Reaction Scheme 6.

REACTION SCHEME 6

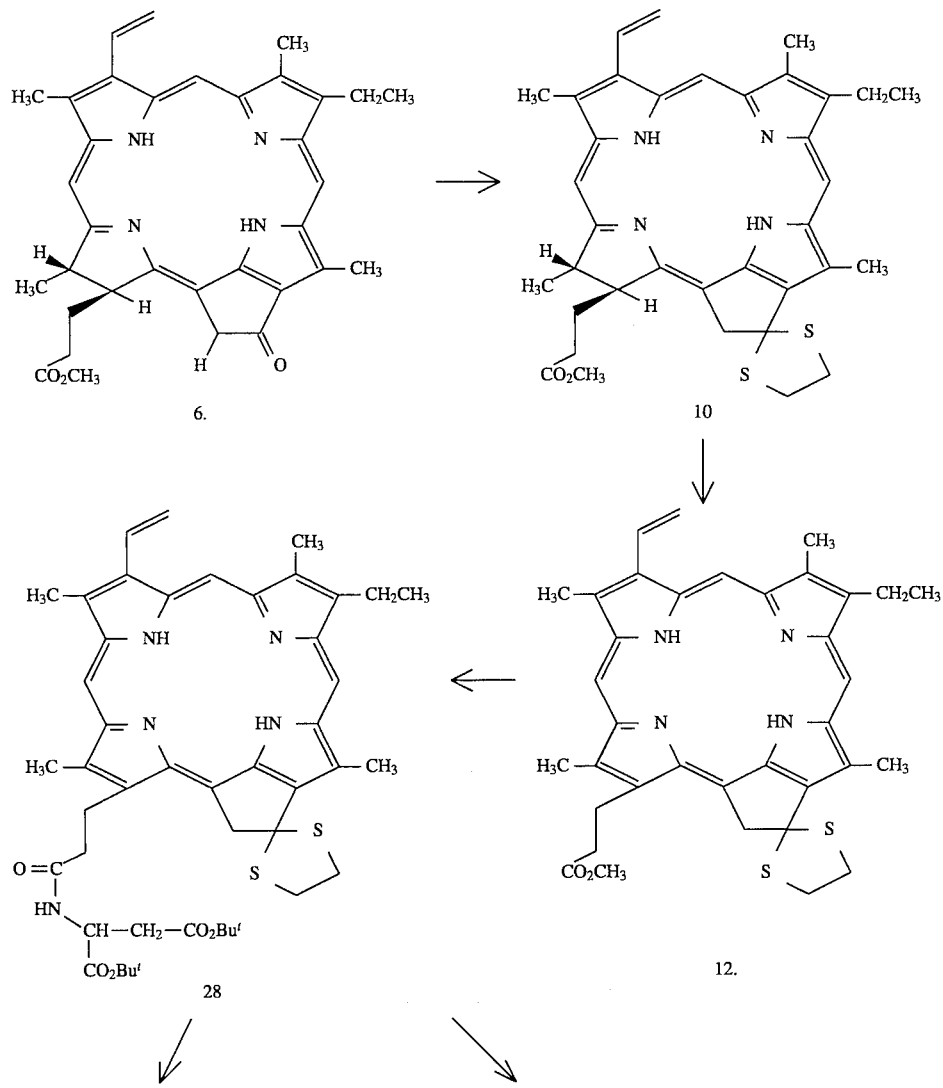

-continued
REACTION SCHEME 6

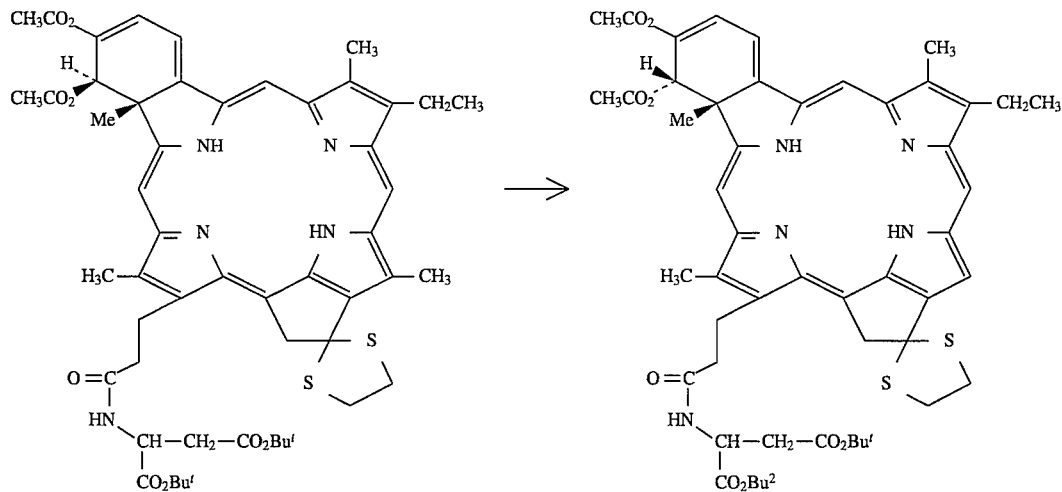

Methyl pyropheophorbide-a (6) is dissolved in a mixture of an organic solvent, preferably in a mixture of methylene chloride, 1,2-ethanedithiol and trimethylsilylchloride (TMS-iCl). Water is then added to the flask containing the mixture and the flask is sealed for about 12–48, preferably for about 24 hours. The mixture is poured into a basic solution, preferably into 5% ammonia, washed, dried, filtered, and evaporated. In order to remove 1,2-ethanediol, the obtained crude product is heated with an alcohol, preferably with isopropyl alcohol. The mixture is heated, boiled and upon cooling, the product is filtered by suction and crystallized using methods known in the art to provide 9-thioketal methyl pyropheophorbide-a (10). Compound (10) is converted to 9-thioketal-2 -vinylphylloerythrin methyl ester (12) by addition of DDQ in benzene to the solution of compound (12) in methylene chloride under stirring at about 0° C. temperature. After about 1–10 preferably 5 minutes of stirring, the mixture is filtered through aluminum and crystallized to give ketal compound (12). Ditertbutylaspartate derivative (28) of compound (12) is prepared by hydrolysis of compound (12) by warming it slowly in a solution of tetrahydrofuran in the presence of a strong base such as 1M potassium hydroxide, for about 1–7, preferably for 3 hours. The mixture is then cooled on an ice bath and neutralized with preferably 2M HCl. The obtained residue is purified and the solid is used to prepare the aspartic acid derivative (28) by reacting it to a di-tert butyl ester of aspartic acid in presence of -1,3-dicyclohexylcarbodiimide (DCC), dimethylaminopyridine (DMAP) and methylene chloride. Compound (28) is then converted to its Diel-Alder adducts cis or trans isomers (30) and (32) by submitting them to Diel-Alder work-up as described above.

Preparation benzoporphyrin derivative cis (23) and trans isomers (21) is illustrated in Reaction Scheme 7.

REACTION SCHEME 7

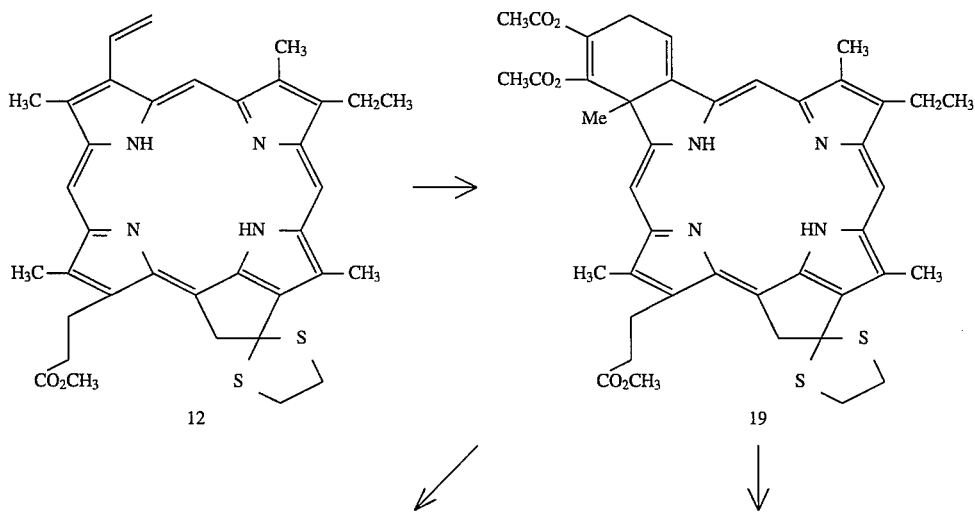

-continued
REACTION SCHEME 7

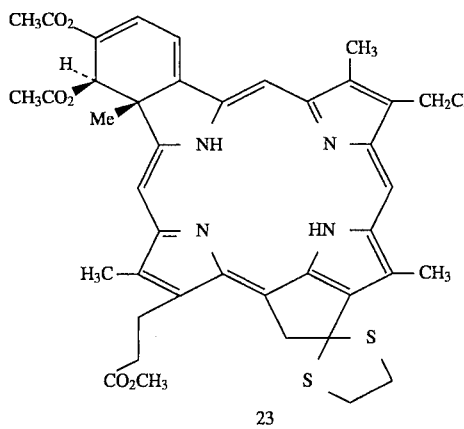

23

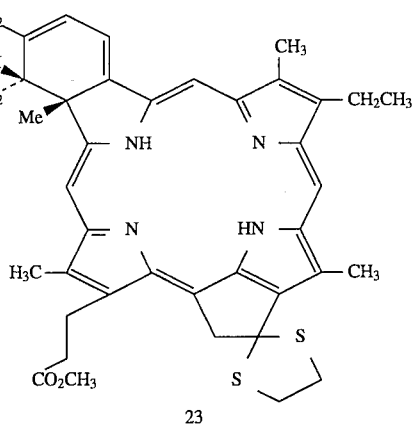

23

Compound (12) described in Reaction Scheme 6 is reacted with DMAD in an organic solvent, preferably in toluene and the reaction mixture is refluxed, as described above for compound (18) and the Diels-Alder product (19) is isolated. Product (9) is treated with an amine, preferably triethylamine for 6–24 hours, preferably overnight. The desired benzoporhyrin trans isomer photosensitizer (21) is isolated by methods described for compound (16).

In alternative, cis isomer benzoporphyrin compound (23) is prepared by reacting the compound with DBU similarly to the preparation of compound (22) described in Reaction Scheme 5.

The Diels-Alder reactions on 2-vinylphylloerythrin methyl ester (13) was hindered by the electron withdrawing ability of the keto group attached to the E-ring. Although the coupling of 2-vinylphylloerythrin methyl ester with tetracyanoethylene (TCE) in refluxing chloroform under nitrogen gave the desired chlorin, no reaction was observed when the less reactive dienophile DMAD was used under similar conditions, or even at elevated temperatures. However, reaction of the 9-glycolketal of 2-vinylphylloerythrin methyl ester (9) with DMAD produced the desired adduct (18), which was then rearranged with triethylamine to give trans isomer (20), which on further treatment with DBU gave the cis isomer (22).

The ethylene glycol ketal group tended to cleave during silica column chromatography. In order to avoid this problem, the keto group of methyl pyropheophorbide-a (6) was protected as the more stable thioketal. The 9-thioketal of methyl pyropheophorbide-a (10) was made in a similar manner as the ethylene glycol ketal, although TMSiCl was unsuccessful at catalyzing the reaction by itself. Consequently, few drops of water were added to a failed refluxed dry reaction and left to decompose the TMSiCl. The HCl produced from the addition of the water proved to be enough to promote the reaction. These dry HCl conditions achieved by excess of TMSiCl, were duplicated and the synthesis of the 9-thioketal of methyl pyropheophorbide-a (10) was accomplished in 82% yield. The 9-thioketal of 2-vinylphylloerythrin methyl ester (12) was synthesized by the addition of about 1.1 equivalents of DDQ in benzene at 0° C. to a $CH_2Cl_2$ solution of the chlorin thioketal over a 3 minute period. Direct DDQ oxidation of the TMSiCl ketalization mixture resulted in extremely low yields. Purification by quickly pouring the cold reaction mixture through a short alumina column with rinses of 1% $MeOH/CH_2Cl_2$, followed by recrystallization from $CH_2Cl_2/MeOH$, gave a greater than 85% yield for each run.

The desired Diels-Alder adduct (19) of the 9-thioketal of 2-vinylphylloerythrin methyl ester was isolated in an overall yield of 40%. The cis isomer (23) obtained by DBU rearrangement has a longer wavelength maximum (675 nm) than the corresponding trans isomer (25) obtained by TEA rearrangement (663 nm).

Since methyl esters are generally not as effective in PDT as aspartate amide derivatives, a number of di-tert butyl BPDs (30), (32) have also been prepared in order to compare their biological activities.

For the preparation of the aspartyl derivatives with the exocylic ring, the aspartyl group was introduced before Diels-Alder reaction and base-promoted rearrangement. Thus, mild KOH hydrolysis of the 9-ketal or thioketal of 2-vinylphylloerythrin methyl ester (11) or (12) followed by aspartate amide linking gave the aspartyl derivatives (28) and (29) in good yield. The ketal (28) was also prepared by an alternate method, in which 2-vinylphylloerythrin methyl ester was hydrolyzed to give 2-vinylphylloerythrin (34), which was then reacted with the aspartic di tert-butyl ester to give compound (35) which was then ketalized in excellent yield.

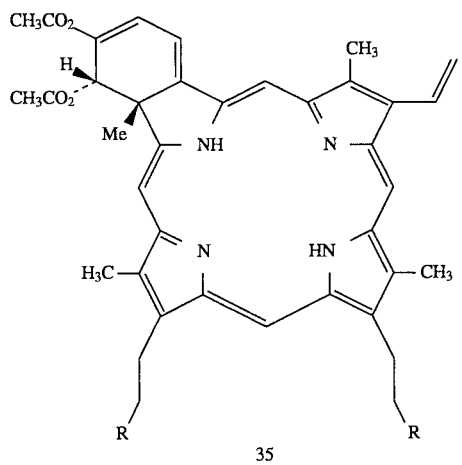

35

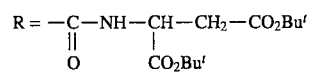

The Diels-Alder coupling of the aspartate derivatives of the ketals (30) and (32) was accomplished by following the procedure as discussed for other benzoporphyrin derivatives, for example, (16) and (17) and these photosensitizers were isolated in good yield.

In alternative, compounds (27) and (28) whether glykolketal or thiolketal can be prepared from carboxylic acids compounds (25) and (26) which are products of methyl esters compounds (11) and (12), as seen in Reaction Scheme 8.

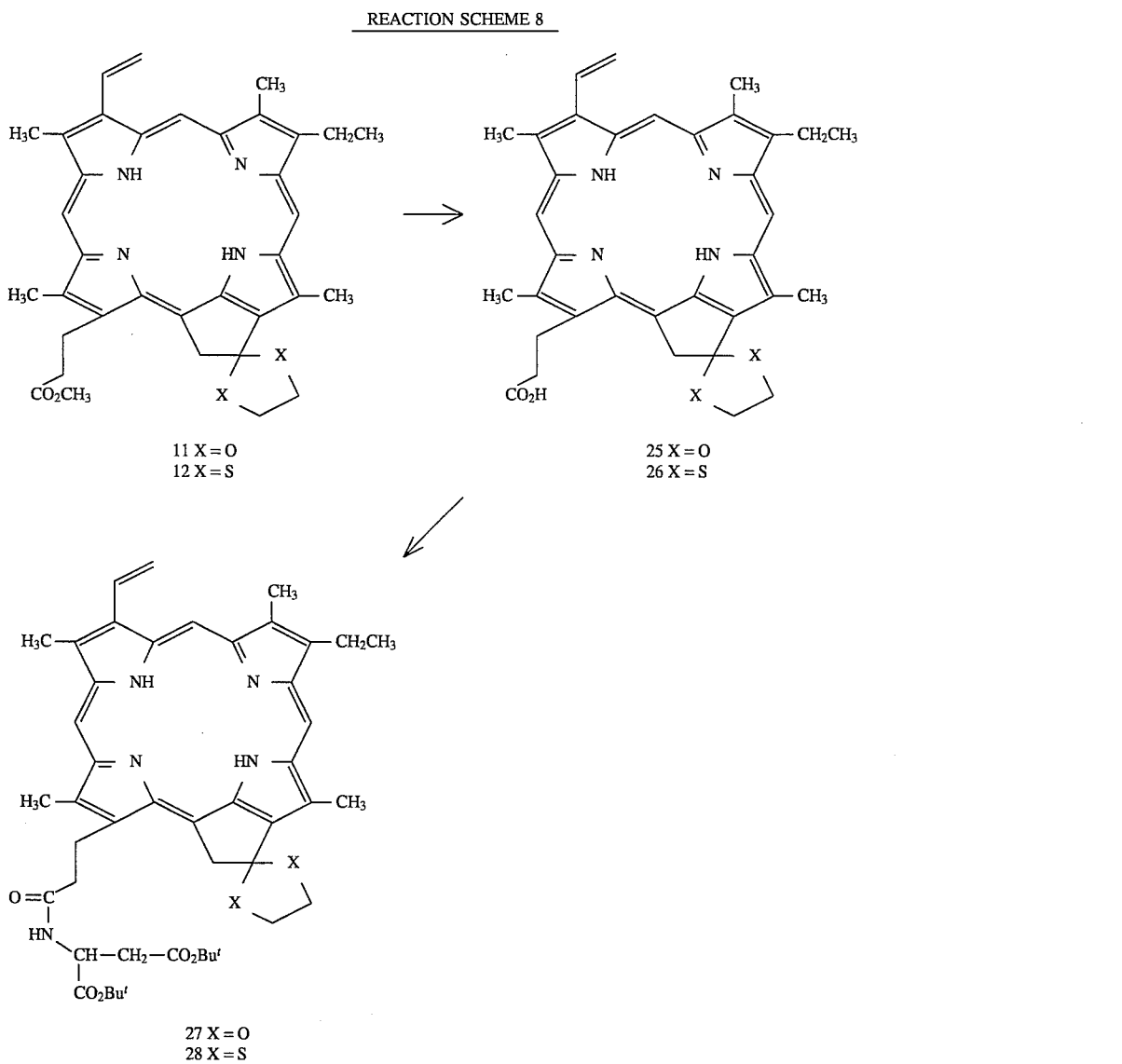

REACTION SCHEME 8

11 X = O
12 X = S

25 X = O
26 X = S

27 X = O
28 X = S

Compounds (25) and (26) and ultimate products (27) and (28) are produced by methods described above.

The addition of the ketal group shifts the soret band (10) to (12) nm to a lower wavelength. The UV spectrum of methyl pyropheophorbide-a (6) compared with the UV spectrum of the 9-glycolketal of methyl pyropheophorbide-a (9) and the UV of 9-glycolketal of 2-vinylphylloerythrin methyl ester (11) was compared to the UV spectrum of 2-vinylphylloerythrin methyl ester and each showed a shift of 12 nm. Also, the intensity of the soret band increases when the chlorin is oxidized.

UTILITY

The higher concentration of porphyrin and phylloerythrin methyl ester related photosensitizers accumulated in malignant tumors is used for the treatment and detection of cancer.

For detection of early stage small tumors, photosensitizer is administered to a patient by i.v. The photosensitizer accumulates in the tumor. Then, the porphyrin-containing tumor cells and surrounding tissues are exposed to light. The porphyrins emit a strong fluorescence, which contrasts with the much weaker fluorescence from the normal tissue, allowing for detection of the tumor.

For the treatment of cancer, PDT consists of injecting the patient with a photoactive dye and irradiating the tumor area with a wavelength of light which activates the dye to produce toxins which kill the tumor. The porphyrin dyes become toxic to the surrounding environment by producing singlet oxygen and other radicals.

PDT techniques depend on whether and how well the compound used concentrates within the tumor cell. Skin photosensitivity is the only known side effect of PDT. Because skin retains these chemicals in enough quantities to produce surface reactions, patients must avoid exposure to sunlight.

The distribution of the photosensitizers of the current invention varies according to the cell type and photosensitizer derivative. Once the photosensitizer is injected intravenously, some of the drug escapes the blood stream and moves into the interstitial fluid. The porphyrin binds to the cellular membrane and slowly diffuses into the cell cytoplasm. Each porphyrin, then, rapidly binds to hydrophobic regions inside the cell. Fluorescence microscopy of porphyrin-treated leukemia L1210 cells shows a localization around the plasma membrane and within the intracellular vesicles.

In vivo biological activity was tested using the method described in *Adv. Exp. Med. Biol.*, 160:3 (1983).

Test results have determined that the thioketal methyl ester is the least toxic, yet some regrowth of tumor has been detected after 20 days. The tumor response data thus far shows that these compounds are all active accept for the glycolketal derivatives which show no activity when eradiation is done on the highest absorbance maximum for the glycolketal. Presumably, the ketal is being hydrolyzed in the body which changes the wavelength needed for excitation. The thioketal BPD tea rearranged is toxic at levels of 0.5 g/kg body weight.

Photosensitizers 15, 17, 21, 22 and 23 of the current invention have been evaluated for in vivo photosensitizing efficacy vis-a-vis commercially available photosensitizer benzoporphyrin derivative (BPD) from QUADRALOGIC Technologies, (QLT), Vancouver, Canada, using the standard screening system of DBA/2 mice bearing transplanted SMT/F tumor according to method described in *Adv. Exp. Med. Biol.*, 160:3 (1983).

Typically, the antitumorigenic activity depended on the dose of the administered photosensitizer and on the time of treatment after i.v. injection of the photosensitizer. When the light treatment was initiated 3 hours after the photosensitizer injection, photosensitizers of the current invention responded with significant tumoricidal activity in reducing number of tumors. When the treatment was initiated 24 hours after photosensitizer administration, there was no response observed. Overall, the photosensitizers of the current invention were approximately 2–3 times as effective as commercially available QLT benzoporphyrin derivative used as control.

Results are summarized in Table 1.

TABLE 1

Biological Activity of Photosensitizers In Vivo

| COMPOUND | DOSE (mg/kg) | TIME (h) (after Inj.) | TUMOR RESPONSE (DAY)*, # | | |
|---|---|---|---|---|---|
| | | | 1–2 | 7 | 30 |
| BPD Controls (QLT Drug) | 5.0 | 24 | 0 | 0 | 0 |
| | 5.0 | 3 | 6/6 | 4/6 | 4/6 |
| | 1.0 | 3 | 2/6 | 0/6 | 0/0 |
| (22) DBU rearranged Ketal (cis) | 1.0 | 3 | 0 | 0 | 0 |
| (23) DBU rearranged thioketal (trans) | 1.0 | 3 | 6/6 | 6/6 | regrowth day 15 |
| (21) Et$_3$N rearranged thioketal (trans) | 1.0 | 3 | All mice died after light treatment | | |
| | 0.5 | 3 | 6/6 | 2/6 | regrowth day 15 |
| (15) BPD from rhodoporphyrin-XV as methyl ester | 1.0 | 3 | No Response | | |
| (17) BPD from rhodoporphyrin-XV as aspartyl derivative | 1.0 | 24 | No Response | | |
| | 1.0 | 3 | 6/6 | 6/6 | 3/6 (Day 80, 3/6) |

*4–6 diameter tumors were exposed to 75 mW/cm$^2$ light for 30 minutes to deliver 135 J/cm$^2$ light from a tunable dye laser tuned to the maximum red absorption peak.
Non-palpable tumors.

As seen from Table 1, commercially available BPD showed significant tumoricidal activity when the mice were treated 3 hours post i.v. injection at a dose 5.0 mg/kg. At similar dose, no tumor response was observed at 24 hours after injecting the drug. At lower dose, (1.0 mg/kg, 3 hours post i.v. injection), it was found to be inactive. The ketal derivative (22) at a dose of 1.0 mg/kg did not show any tumor response. However, the thioketal analogue (22) at the same dose (1 mg/kg) was found to be more active than BPD. Surprisingly, the trans isomer compound (21) at a dose of 1.0 mg/kg was found to be toxic and all mice died after the light treatment. At a lower dose (0.5 mg/kg), compound (21) showed much better photosensitizing activity than BPD. At 0.5 mg/kg dose, all tumor responded within 1–2 days following the treatment, 30% of tumors responded at day 7 following the treatment. Regrowth of the tumor started around day 15.

Among BPDs obtained from rhodoporphyrin series some promising results were obtained. For example, the BPD methyl ester (15), was found to be inactive at a dose of 1.0 mg/kg. On the other hand the di-tert-butyl aspartyl derivative (17) showed excellent photosensitizing activity at similar conditions. In response to the light treatment initiated 3 hours after the injection, there was 100% tumor response both at days 1–2 and 7 and 50% at day 30 and longer. These results suggest that there is a significant increase in antitumor activity by replacing methyl esters with di-tert butyl aspartyl groups. Based on the above results, a series of aspartyl derivatives seen in Reaction Schemes 1 and 8 were synthesized and tested.

Similarly, an isomerically pure BPD type photosensitizers prepared by rhodoporphyrin-XV dimethyl ester were tested for their photosensitizing activity. The new photosensitizers have much stronger efficacy than control BPD.

When the effect of compound (17) di-tert-butyl was compared to commercially available BPD, as seen in Table 2, much improved activity was observed at the low dose of 1 mg/kg of administered photosensitizer followed by treatment 3 hours later. There was 100% tumor response observed in the experimental group up to 30 days. From 30 days, there was 50% response observed while there was only 30% response observed at days 1–2 in control BPD group and response beyond that period.

TABLE 2

Biological Activity of Rhodoporphyrin - XV Dimethyl Ester

| STRUCTURE | DOSE (mg/kg) | TIME (h) BETWEEN INJECTION & LIGHT TREATMENT | TUMOR RESPONSE (d)*, # | | | | |
|---|---|---|---|---|---|---|---|
| | | | 1–2 | 7 | 15 | 30 | 80 |
| Control | 5.0 | 24 | 0 | 0 | 0 | 0 | 0 |
| BPD (QLT Drug) | 5.0 | 3 | 6/6 | 4/6 | 4/6 | 4/6 | 0/6 |
| (Mixture of isomers) | 1.0 | 3 | 2/6 | 0/6 | 0/6 | 0/6 | 0/6 |
| (17) | 1.0 | 3 | 6/6 | 6/6 | 6/6 | 3/6 | 3/6 |

*4–6 diameter tumors were exposed to 75 MW/cm$^2$ for 30 minutes to deliver 135 J/cm$^2$ from a tunable dye laser tuned to the maximum red absorption peak.
Non-palpable tumors.

METHODS AND MATERIALS

Characterization of Compounds:

Melting points (MP) (uncorrected) were measured on a Thomas/Bristoline microscopic hotstage apparatus.

Ultra violet Light Spectra (UV-Vis): Electronic absorption spectra were measured on a Hewlett-Packard 8450A spectrophotometer using solutions in dichloromethane unless otherwise stated.

Mass spectra (MS) were obtained at the Facility for Advanced Instrumentation at the University of California, Davis, on a VG Analytical ZAB-HS-2F mass spectrometer, using a direct insertion probe.

EI spectra were acquired with 70 eV, 50 mA and a source temperature of 200° C.

Nuclear Magnetic Resonance 1 H NMR: Proton NMR spectra were obtained at 300 MHz on a General Electric QE-300 spectrometer. Samples were dissolved in CDCl$_3$ and chemical shifts are reported relative to CHCl$_3$ at 7,258 ppm unless stated otherwise.

CHN Analysis: Elemental analyses were determined by the Microanalytical Laboratory at the University of California, Berkeley.

Chromatographic Methods:

Thin Layer Chromatography (TLC): Analytical thin-layer chromatography was used to monitor reactions and check purity of eluents from columns on cut strips (ca. 2 cm×6 cm) of Merck or Whatman silica gel 60 F254 precoated (0.25 mm thickness) plastic-backed sheets. Preparative TLC was performed on freshly prepared glass plates (20 cm×20 cm) coated with ca. 2 mm thick Merck silica gel GF 254. Plates were activated prior to use by heating to 110° C. for at least 8 hours. Column Chromatography (CC): Two types of packing were used:

(i) Alumina (70–230 mesh) was deactivated with 6% H2O (Brockmann Grade III) before use.

(ii) Silica gel 60 (70–230 mesh) was used for normal gravity chromatography and silica gel 60 (230–400 mesh) was used for flash chromatography. Pressure for the later was supplied by house compressed air.

Analytical HPLC: High Pressure Liquid Chromatography (HPLC): HPLC was performed using a Waters Associates 600E system controller equipped with a Rheodyne injector, and a 490E programmable multi-wavelength detector set at 405 nm. The separation profiles were recorded using a Fisher series 5000 chart recorder. Normal-phase separations were carried out on a Waters RCM 8×10 Radial pack Bondpak 10u silica. The solvent systems are discussed for specific cases in the text. All solvents were reagent grade and were filtered through a 0.45 um Millipore filter before use. Degassing was accomplished by stirring for several minutes under house vacuum after mixing solvents. Samples were filtered through a 0.45 um filter prior to injection.

Purification of Solvents:

Acetonitrile: Distilled over calcium hydride.

Dichloromethane: Distilled over calcium hydride.

Toluene: Distilled over calcium hydride.

All other solvents were used as commercially available.

The phrase "dried, filter and evaporated" means drying over sodium sulfate, filtering through glass wool, and then evaporating off the volatile solvent using a Buchi rotary evaporator under house vacuum or high vacuum achieved with an oil pump.

EXAMPLE 1

Preparation of Rhodoporphyrin Dimethyl Ester (8)

This example illustrates preparation of preparation of rhodoporphyrin dimethyl Ester (8).

Rhodochlorin dimethyl ester (7) (176 mg, 0.3 mmole) was dissolved in dichloromethane (100 ml) to which was added 50 mg DDQ in benzene (10 ml) dropwise. The mixture was stirred at room temperature for 10 min., and is passed through short alumina (grade III) column. The eluates are collected, washed with water. The organic layer was separated, dried over anhydrous sodium sulfate, and evaporated to dryness. The residue was purified by column chromatography (alumina, grade III), eluting with dichloromethane. The appropriate eluates were collected. The residue obtained after evaporating the solvent was crystallized from dichloromethane/hexane in 69% yield (120 mg) of rhodoporphyrin dimethyl ester (8).

λ Max (in CH$_2$Cl$_2$): 668 (2630); 636 (3680); 576 (12, 660); 552 (20,890); 512 (11, 820); 404 170, 000).

NMR (ppm): 10.99.

10.09, 10.04 and 9.91 (each s, 1H, 4 Meso H); 8.20 (d, 1H, J=12.6 Hz, CH=CH$_2$); 6.32, 6.12 (each d, 1H, J=19.6 Hx, CH=CH$_2$); 4.46, 3.94, 3.70, 3.64, 3.63 and 3.62 (each s, 3H, 6 CH$_3$); 4.44 (t, 2H, J=9 Hz, CH$_2$CH$_2$CO$_2$); 4.09 (q, 2H, J=8 Hz, CH$_2$CH$_3$); 3.37 (t, 2H, J=9 Hz, CH$_2$CH$_2$CO$_2$); 1.86 (t, 3H, J=8 Hz, CH$_2$CH$_3$); −4.01 (br s, 2H, 2 NH). Mp.265° C.

EXAMPLE 2

Preparation of Benzoporphyrins (15) and (16)

This example illustrates preparation of benzoporphyrins (15) and (16).

Rhodoporphyrin dimethyl ester (8) (135 mg, 0.24 mmole), dissolved in dimethylacetylene decarboxylate (1 ml), along with toluene (40 ml) were refluxed under nitrogen for 60 hours. The solvents were removed under high vacuum, and the residue was purified by column chromatography (alumina, grade III), eluting with dichloromethane- The red brown fraction was evaporated to give the intermediate Diels-Alder adduct (14) in 40% yield.

λ Max (in CH$_2$Cl$_2$): 646 (21,140); 590 (13,870); 556 (21,830); 528 (14,350); and 414 (148,000).

NMR (ppm, CDCl$_3$): 10.78, 9.81, 9.26, and 9.01 (each s, 1H, 4 Meso H); 7.42 (d, 2H, J=6.0 Hz, exocyclic ring CH$_2$); 7.34 (m, 1H, exocyclic ring CH); 4.36, 4.04, 3.92, 3.79, 3.72, 3.49 and 3.46 (each s, 3H, 7 CH$_3$); 4.34 (t, 2H, J=8 Hz, CH$_2$CH$_2$CO$_2$); 3.98 (q, 2H, J=8 Hz, CH$_2$CH$_3$); 2.10 (s, 3H, 1-CH$_3$), 1.81 (s, 3H, J=8 Hz, CH$_2$CH$_3$), −2.26 (br s, 1H, NH); −2.25 (br s, 1H, NH).

Mp. 130° C.

Intermediate Diels-Alder adduct (14) was dissolved in dichloromethane (50 ml) and triethylamine (1 ml) was added. The reaction mixture was stirred at room temperature for 3 hours. The green solution was then evaporated to dryness to give trans isomer (16) in almost quantitative yield.

λ Max (in CH$_2$Cl$_2$): 662 (8041), 584 (12,300); 434 (42, 770); NMR (ppm, in CDCl$_3$): 10.71, 9.73, 9.13 and 9.10 (each s, i H, 4 Meso H); 7.68 (dd, 1H, J=6.0, 3.0 Hz, exocyclic ring vinyl-CH); 4.70 (d, 1H, J=6 Hz, exocyclic ring vinyl-CH); 4.35, 4.24, 3.95, 3.74, 3.70, 3.44 and 3.37 (each s, 3H, 7 CH$_3$); 4.31 (q, 2H, J=7.7 Hz, CH$_2$CH$_3$); 3.90 (t, 2H, J=7.7 Hz, CH$_2$CH$_2$CO$_2$)' 4.25 (t, 2H, J=7.7 Hz, CH$_2$CH$_2$CO$_2$); 1.75 (t, 3H, J=7.6 Hz, CH$_2$CH$_3$); 1.58 (s, 3H, 1-CH$_3$); −2.43 (br s, 1H, NH ); −2.45 (br s, 1H, NH).

Mp. 242° C.

For the synthesis of cis isomer benzoporphyrin dimethyl ester (15), the intermediate (14) was dissolved in dichloromethane (30 ml) and DBU (10 drops) was added to it. The reaction mixture was stirred under nitrogen for 10 min. The green solution was evaporated and the residue was chromatographed on alumina (grade III) column, eluting with dichloromethane. Evaporation of the solvent and crystallization with CH$_2$Cl$_2$/hexane gave the desired product benzoporphyrin dimethyl ester (15) in 40% overall yield.

λ Max (in CH$_2$Cl$_2$): 668 (24, 300); 608 (27,070); 592 (31, 110); and 438 (97, 800).

NMR (ppm, in CDCl$_3$): 10.75, 9.84, 9.32, 8.93 (each s, 1H, 4 Meso H); 7.86 (d, 1H, J=6.0 Hz, exocyclic ring vinyl CH); 7.48 (d, 1H, J=6.0 Hz, exocyclic ring vinyl CH); 4.39, 4.04, 3.81, 3.75, 3.50, 3.47 and 3.05 (each s, 3H, 7 CH$_3$); 4.32 (t, 2H, J=9 Hz, CH$_2$CH$_2$CO$_2$); 4.02 (q, 2H, J=8 Hz, CH$_2$CH$_3$); −2.01 (br s, 1H, NH); −1.99 (br s, 1H, NH). Analysis calculated for C$_{40}$H$_{42}$N$_4$O$_8$+1. H$_2$O: C, 67.10; H, 6.06; N, 7.83. Found: C, 66.94; H, 6.07; N, 7.91.

Mp. 265° C.

EXAMPLE 3

Preparation of Benzoporphyrin Derivative

This example illustrates preparation of preparation of Diels-Alder adduct benzoporphyrin cis isomer derivative (17).

Benzoporphyrin dimethyl ester (15) (135 mg) was dissolved in tetrahydrofuran (10 ml) to which was added 25% aqueous HCl (10 ml). The reaction was stirred overnight, and after the usual work up the solvent was evaporated. The residue was purified on a short silica column, eluting with 5% methanol in dichloromethane. The appropriate eluates were collected, the solvent was evaporated and the intermediate carboxylic acid residue was crystallized from CH$_2$Cl$_2$/hexane in 64% yield (85 mg).

λ Max (CH$_2$Cl$_2$): 670 (18, 910); 608 (20, 420); 592 (23, 760), 438 (80, 800).NMR (ppm, in CDCl$_3$): 10.72, 9.78, 9.30 and 8.91) each s, 1H, 4 Meso H); 7.84 (d, 1H, J=5.6 Hz, exocyclic ring vinyl CH); 7.46 (d, 1H, d, J=5.6, exocyclic ring vinyl CH); 5.08 (s, 1H, exocyclic CHCO$_2$CH$_3$); 4.33, 4.01, 3.76, 3.48, 3.43, 3.03 (each s, 3H, 6 CH$_3$); 4.26 (t, 2H, J=8.6 Hz, CH$_2$CH$_2$CO$_2$CH$_3$); 1.83 (s, 3H, 1-CH$_3$); 1.77 (t, 3H, J=8 Hz, CHCH$_3$), −2.03 (br s, 2H, 2NH). HRMS, Calculated for C$_{39}$H$_{40}$N$_4$O$_8$: M+=692.2840, Found, 692.2843.

Mp. 268° C.

The intermediate carboxylic acid so obtained (45 mg, 0,065 mmole) was dissolved in dichloromethane (10 ml). Dicyclohexylcarbodiimide (DCC) [50 mg], dimethylaminopyridine (DMAP) [5 mg] and aspartic acid di tert butyl ester (50 mg) were added and the reaction mixture was stirred overnight at room temperature under inert atmosphere. The solution was then diluted with dichloromethane (100 ml), washed with water. The organic layer was separated, dried over anhydrous sodium sulfate. Evaporation of the solvent gave a residue which was purified by preparative silica plates, eluting with 5% methanol in dichloromethane, and the desired benzoporphyrin photosensitizer (17) was obtained in 65% yield (39 mg).

λ Max (in CHCl$_2$): 670 (20, 580); 608 (22, 370); 592 (25, 390), 440 (85, 600).

NMR (ppm, in CDCl$_3$): 10.72, 9.79, 9.28 and 8.99 (each s, 1H, 4 MesoH); 7.82 (d, 1H, J=6.0H, exocyclic ring vinyl CH); 7.44 (d, 1H, J=6.0 Hz, exocyclic ring vinyl CH); 6.62 [m, 1H, NH(CO)], 5.06 (s, 1H, exocyclic ring CHCO$_2$CH$_3$); 4.82 (m, 1H, CH CO$_2$CH$_3$); 4.36, 3.99, 3.77, 3.45, 3.42 and 3.02 (each s, 3H, 6 CH$_3$); 4.32 (t, 2H, CH$_2$CH$_2$CO$_2$); 3.97 (q, 2H, J=8.3 Hz, CH$_2$ CH$_3$); 3.19 (m, 2H, CH$_2$CH$_2$CO$_2$); 2.82 (dt, 1H, aspartic CH$_2$CO$_2$); 2.63 (dt, 1H, aspartic CH$_2$CO$_2$); 1.80 (s, 3H, 1-CH$_3$); 1.77 (t, 3H, J=8.3 Hz, CH$_2$CH$_3$), 1.60 (br s, 3 H, CH$_3$); 1.38, 1.35, 1.10, 1.09 (each s, 3H, 4 CH$_3$); 0.87 (q, 3H, J=8 Hz, CH$_3$); −2.01, −2.07 (each br s, 1H, 2 NH).

HRMS calculated for $C_{51}H_{61}N_5O_{11}$: M+=919. 4359; Found, 919.4360, Analysis calculated for $C_{51}H_{61}N_5O_{11}$: C, 66.57; H, 6.69, N, 7.61; Found: C, 65.23, H, 6.79, N, 7.07.
Mp. 125° C.

EXAMPLE 4

Preparation of 9-Glycolketal of Methyl Pyropheophorbide-a (9)

This example illustrates preparation of preparation of 9-glycolketal of methyl pyropheophorbide-a (9).

Methyl pyropheophorbide-a (6) (2.5 g) in dry $CH_2Cl_2$ (500 ml) was stirred under nitrogen and ethylene glycol (2 ml) and trimethylsilyl chloride (2 ml) were added. The reaction was stirred for 12 hours. The reaction was reduced in temperature in a dry ice isopropanol bath (−27° C.) and then poured into a 1N $NH_4OH$ solution to which some residual ice was added (≈−60° C.). This mixture was partitioned, and the $CH_2Cl_2$ layer is washed, dried, filtered and evaporated to dryness. The bright green residue was eluted (100% $CH_2Cl_2$) through an alumina column. The lighter green fraction was recrystallized from $CH_2Cl_2$/MeOH to give the title 9-glycolketal of methyl pyropheophorbide-a (9) compound (2.35 g, 88%) as bright green crystals.

Mp: 173°–176° C.

λ Max nm (e): 400 (163,300), 500 (19,800), 550 (6,600), 598 (9,350), 652 (49,700).

1H NMR: 9.70, 9.65 (each s, 2×1H, a and b Meso H), 8.75 (s, 1H, d Meso H), 8.00 (dd, 1H, 2a-CH, J=18,12), 6.28 (d, 1H, 2b-CH trans to 2a-CH, J=18), 6.17 (d, 1H, 2b-CH cis to 2a-CH,J=12), 5.09 (ABq, 2H, 10-$CH_2$, J=21,27), 4.70–4.40 (m, 5H, 8-H and 9-O—$CH_2CH_2$—O), 4.35 (m, 1H, 7-H), 4.00 (q, 2H, 4a-$CH_2$), 3.60, 3.54, 3.44, 3.40 (each s, 4×3H, 1-Me, 3-Me, 5-Me and 7-OMe), 2.80–2.20 (m, 4H, 7-$CH_2CH_2$), 1.80 (d, 3H, 8-Me), 1.69 (t, 3H, 4b-Me), −1.12, −3.09 (each br s, 2×1H, NH).

Anal. Calcd. for $C_{36}H_{40}N_4O_4.H_2O$: C 70.80 H 6.93 N 9.17. Found:C 71.09 H 6.67 N 9.02.

EXAMPLE 5

Preparation of 9-Thiolketal of Methyl Pyropheophorbide-a (10)

This example illustrates preparation of preparation of 9-thiolketal of methyl pyropheophorbide-a (10).

Methyl pyropheophorbide-a (6) (1.45 g) was dissolved in $CH_2Cl_2$ (200 ml) and 1,2-ethanedithiol and trimethylsilyl chloride TMSiCl (each at 1.5 ml) were added. Water (10 drops) was added so that dry HCl was produced in the flask, which was then sealed for 24 hours. This mixture was poured into 5% ammonia solution, washed with brine, dried, filtered and evaporated to dryness. The crude product mixture was heated with isopropyl alcohol, which only partially dissolved the porphyrin, but allowed leaching out of the excess 1,2-ethanedithiol, which tends to interfere with the column purification.

After heating the mixture to a boiling, while scraping the sides of the flask to loosen the solid, the flask was cooled and the solid was filtered by suction. The solid was then heated with petroleum ether in a similar manner, cooled and filtered. The obtained crystals were eluted through an alumina (Brockmann Grade III) column using 0.25% methanol/2% THF in $CH_2Cl_2$ as elutant. The fastest-running light green product was collected, evaporated to dryness, and crystallized from $CH_2Cl_2$/isopropyl alcohol by slowly evaporating off of the $CH_2Cl_2$ from the solvent mixture at room temperature under vacuum. The crystals were filtered and rinsed with petroleum ether to remove excess isopropanol to give a blue-green powder of 9-thioketal of methyl pyropheophorbide-1 (10) (1.12 g, 76%).

Mp: 121°–123° C.

λ Max nm (e): 408 (78,731), 506 (10,528), 600 (4,625), 652 (22,130).

1H NMR: 9.88, 9.67 (each s, 2×1H, a and b Meso H), 8.91 (s, 1H, d Meso H), 8.23 (dd, 1H, 2a-CH, J=18, 12), 6.39 (d, 1H, 2b-CH trans to 2a-CH, J=18), 6.20 (d, 1H, 2b-CH cis to 2a-CH, J=12), 5.65 (ABq, 2H, 10-$CH_2$, J=21, 27), 4.84 (q, 2H, 4a-$CH_2$),4.67 (m, 1H, 8-H), 4.42 (m, 1H, 7-H), 3.97 (m, 4H, 10-S—$CH_2CH_2$—S), 3.67, 3.63, 3.58, 3.42 (each s, 4×3H, 1-Me, 3-Me, 5-Me and 7-OMe), 2.8–2.2 (m, 4H, 7-$CH_2CH_2$), 1.86 (d, 3H, 8-Me), 1.77(t, 3H, 4b-Me), −1.26, −3.19 (each br s, 2×1H, NH). Anal. Calcd. for $C_{36}H_{40}N_4O_2S_2$: C 69.42 H 6.15 N 9.00. Found: C 67.50 H 6.35 N 8.80.

EXAMPLE 6

Preparation of 9-Glycolketal of 2-Vinyl-Phylloerythrin Methyl Ester (11)

This example illustrates preparation of preparation of 9-glycolketal of 2-vinyl phylloerythrin methyl ester (11).

The 9-glycolketal of methyl pyropheophorbide-a (9) (51 mg) was stirred in $CH_2Cl_2$ (30 ml) at 0° C. while DDQ (220 mg) was added. After 3 minutes, the mixture was forced through a small pad of alumina. The solid was recrystallized from $CH_2Cl_2$/n-hexane to give the 9-glycolketal of 2-vinyl phylloerythrin methyl ester (11) compound (42 mg, 82%) as a pink dust.

Mp: >300° C. (Lit. 49°>300° C.).

λ Max nm (e): 406 (224,500), 508 (20,800), 544 (16,600), 570 (15,400), 622 (9,600).

1H NMR: 10.01, 9.94, 9.87 (each s, 3×1H, a, b and d Meso H), 8.17 (dd, 1H, 2a-CH, J=18,12), 6.26 (d, 1H, 2b-CH trans to 2a-CH, J=18), 6.07 (d, 1H, 2b-CH cis to 2a-CH, J=12), 5.69 (s, 2H, 10-$CH_2$), 4.68 (m, 4H, 10-O—$CH_2CH_2$—O), 4.28 (t, 2H, 7a-$CH_2$), 4.05 (q, 2H, 4a-$CH_2$), 3.73, 3.68, 3.57, 3.56, 3.54 (each s, 4×3H, 1-Me, 3-Me, 5-Me, 7-oMe and 8-Me), 3.1 (t, 2H, 7b-$CH_2$), 1.82 (t, 3H, 4b-Me), −3.03, −3.85 (each br s, 2×1H, NH).

Anal. Calcd. for $C_{36}H_{38}N_4O_4.H_2O$: C 71.03 H 6.62 N 9.20. Found: C 71.28 H 6.47 N 9.22.

EXAMPLE 7

Preparation of 9-Thioketal of 2-vinylphylloerythrin Methyl Ester (12)

This example illustrates preparation of 9-thioketal of 2-vinylphylloerythrin methyl ester (12).

The 9-thioketal of methyl pyropheophorbide-a (10) (1.0 g) was stirred in $CH_2Cl_2$ (50 ml) at 0° C. while DDQ (350 mg) in benzene (20 ml) was added. After 3 minutes the reaction mixture was forced through a small pad of alumina with 1%MeOH/$CH_2Cl_2$ as elutant. After evaporation to dryness, the red solid was recrystallized from $CH_2Cl_2$/ MeOH to give the 9 -thioketal of 2-vinylphylloerythrin methyl ester (12) compound (0.93 g, 93%) as a pink-red powder.

Mp: 120°–121° C.

λ Max nm (e): 408 (224,100), 508 (22,900), 546 (17,600), 570 (16,350), 620 (10,300).

1H NMR: 10.03, 9.97, 9.92 (each s, 3×1H, a, b and d Meso H), 8.20 (dd, 1H, 2a-CH, J=18, 12), 6.25 (d, 1H, 2b-CH trans to 2a-CH, J=18), 6.10 (d, 1H, 2b-CH cis to 2a-CH, J=12), 6.25 (s, 2H, 10-CH$_2$), 4.37 (t, 2H, 7a-CH$_2$) 4.1–4.0 (m, 6H, 4a-CH$_2$, and 10-S—CH$_2$CH$_2$—S), 3.59, 3.59, 3.59, 3.73, 3.76 (each s, 5×3H, 1 -Me, 3 -Me, 5 -Me, 7 -OMe and 8-Me), 3.10 (t, 4H, 7b-CH$_2$), 1.84 (t, 3H, 4b-Me), −3.01, −3.85 (each br s, 2×1H, NH). Anal. Calcd. for C$_{36}$H$_{38}$N$_4$O$_2$S$_2$: C 69.42 H 6.15 N 9.00. Found: C 68.03 H 6.09 N 8.41.

EXAMPLE 8

Preparation of 2-Vinylphylloerythrin Methyl Ester (13)

This example illustrates preparation of preparation of 2-vinylphylloerythrin methyl ester (13).

The 9-glycolketal of 2-vinylphylloerythrin methyl ester (11) (350 mg) was dissolved in tetrahydrofurane (THF) (100 ml) and acetone (50 ml) and 1M HCl (20 ml) was added while the flask was warmed. The mixture was stirred for 10 minutes. Then CH$_2$Cl$_2$ was added and the organic layer was washed, dried, and evaporated to dryness. The red residue was recrystallized from CH$_2$Cl$_2$/MeOH to give the 2-vinylphylloerythrin methyl ester (13) compound (318 mg, as a red powder.

Mp: 279°–281° C.

λ Max nm (e): 406 (194,000), 508 (19,400), 544 (15,700), 570 (15,000), 622 (9,500).1H NMR: 9.90, 9.83, 9.52 (each s, 3×1H, a, b and d Meso H), 8.18 (dd, 1H, 2a-CH, J=18,12), 6.30 (d, 1H, 2b-CH trans to 2a-CH, J=18), 6.19 (d, 1H, 2b-CH cis to 2a-CH, J=12), 5.47 (s, 2H, 10-CH$_2$), 4.05 (q, 2H, 4a-CH$_2$), 3.96 (t, 2H, 7a-CH$_2$), 3.73, 3.80, 3.61, 3.58, 3.42 (each s, 5×3H, 1-Me, 3-Me, 5-Me, 7-OMe, and 8-Me), 2.90 (t, 2H, 7b-CH$_2$), 1.86 (t, 3H, 4b-Me), −3.1, −3.3 (each br s, 2×1H, NH).

EXAMPLE 9

Preparation of 2-Vinyl Phylloerythrin (33)

This example illustrates the preparation of 2-vinyl phylloerythrin (33).

The methyl ester of 2-vinylphylloerythrin (13) (300 mg) was hydrolyzed in THF (300 ml) and 1M KOH (40 ml). After the addition of HCl and cooling, a precipitate formed. After filtration and rinsing, the red solid was found to be the 2-vinyl phylloerythrin (33) compound (290 mg, 96%). This is used without extensive analysis to make the ditertbutyl aspartate derivative.

Mp: >300° C.

λ Max nm (relative areas) in pyridine/CH$_2$Cl$_2$: 420 (100), 476 (9.2), 524 (10.0), 566 (15.4), 590 (13.1), 640 (7.3).

1H NMR (in pyridine as solvent): 10.25, 10.09, 9.84 (each s, 3×1H, a, b, and d Meso H), 5.76 (s, 2H, 10-CH$_2$), 4.10–3.99 (t, 2H, 7a-CH$_2$, and 2xq, 2×2H, 2a-CH$_2$ and 4a-CH$_2$), 3.85, 3.54, 3.49, 3.43 (each s, 4×3H, 1-Me, 3-Me, 5-Me, and 8-Me), 3.20 (t, 2H, 7b-CH$_2$), 1.88, 1.80 (each t, 2×3H, 2b-Me and 4b-Me), −2.40, −3.65 (each br s, 2×1H, NH).

EXAMPLE 10

Preparation of 2-Vinyl phylloerythrin Di-tert-butylaspartate Derivative (34)

This example illustrates preparation of 2-vinyl phylloerythrin ditertbutylaspartate derivative (34).

2-Vinylphylloerythrin (33) (252 mg) was mixed as described in Example 9. After work up, the crude product was passed through a short pad of alumina with 2% MeOH/ CH$_2$Cl$_2$ as a rinse. The filtered mixture was evaporated to dryness and recrystallized from CH$_2$Cl$_2$/MeOH to give the 2-vinyl phylloerythrin ditertbutylaspartate derivative (34) compound (185 mg, 70%) as a red dust.

Mp: 221°–223° C.

λ Max nm (e): 418 (208,290), 524 (19,600), 566 (28,400), 590 (23,500), 640 (2,300).

1H NMR: 9.90, 9.83, 9.52 (each s, 3×1H, a, b and d Meso H), 8.18 (dd, 1H, 2a-CH, J=18,12), 6.45 (d, 1H, ASP N-H), 6.30 (d, 1H, 2b-CH trans to 2a-CH, J=18), 6.19 (d, 1H, 2b-CH cis to 2a-CH, J=12), 5.14 (s, 2H, 10-CH$_2$), 4.75 (X of ABX, 1H, Asp-CH), 4.05 (q, 2H, 4a-CH$_2$), 3.96 (t, 2H, 7a-CH$_2$), 3.73, 3.80, 3.61, 3.58, 3.42 (each s, 5×3H, 1-Me, 3-Me, 5-Me, 7-OMe, and 8-Me), 2.60 (t, 2H, 7b-CH$_2$), 2.68, 2.35 (ABX, 2H, Asp-CH$_2$), 1.86 (t, 3H, 4b-Me), 1.42, 1.17 (ea s, 2×9H , both O-t-butyl), −3.1, −3.3 (each brs, 2×1H, NH).

Anal. Calcd. for C$_{45}$H$_{57}$N$_5$O$_6$: C 70.75 H 7.22 N 9.17. Found: C 70.44 H 6.97 N 9.17.

EXAMPLE 11

Preparation of 9-Thioketal of 2-Vinylphylloerythrin Di-tert-butylaspartate Derivative (28)

This example illustrates the preparation of 9-thioketal of 2-vinylphylloerythrin di-tert-butylaspartate derivative (28).

The methyl ester of 2-vinylphylloerythrin thioketal methyl ester (12) (255 mg) was hydrolyzed by warming in THF (200 ml) and 1M KOH (10 ml) gently for 3 hours. This was cooled in an ice bath before 2M HCl (20 ml) was added. A solid green-brown residue formed, which was filtered and dried with intermediate rinses of petroleum ether. This solid compound (27) was used directly in the general aspartic acid coupling reaction using Asp (200 mg), DCC (200 mg), DMAP (20 mg), and CH$_2$Cl$_2$ (50 ml). After work-up, the solid was recrystallized with CH$_2$Cl$_2$/MeOH to give the 9-thioketal of 2-vinylphylloerythrin di-tert-butylaspartate derivative (28)compound as a green dust (210 mg, 76%).

Mp: >300° C.

λ Max nm (e): 408 (220,000), 508 (22,000), 546 (17,000), 570 (16,000), 620 (10,000).

1H NMR: 10.30, 10.10, 10.07 (each s, 3×1H, a, b and d Meso H), 8.23 (dd, 1H, 2a-CH, J=18,12), 6.62 (d, 1H, ASP N-H), 6.32 (d, 1H, 2b-CH trans to 2a-CH, J=18), 6.07 (d, 1H, 2b-CH cis to 2a-CH, J=12), 6.26 (s, 2H, 10-CH$_2$), 4.90 (X of ABX, 1H, Asp-CH), 4.40 (t, 2H, 7a-CH$_2$), 4.15 (q, 2H, 4a-CH$_2$), 4.04 (m, 4H, 10-S—CH$_2$CH$_2$—S), 3.78, 3.75, 3.68, 3.66 (each s, 4×3H, 1-Me, 3-Me, 5-Me, and 8-Me), 3.20 (t, 2H, 7b-CH$_2$), 2.80–2.60 (ABX, 2H, Asp-CH$_2$), 1.82 (t, 3H, 4b-Me), 1.42, 1.17 (ea s, 2×9H , both O-t-butyl), −3.00, −3.85 (each br s, 2×1H, NH).

EXAMPLE 12

Preparation of 9-Glycolketal- 2-Vinylphylloerythrin 7-Di-tert-butylaspartate Derivative (27).

This example illustrates preparation of 9-glycolketal-2-vinylphylloerythrin 7-di-tert-butylaspartate derivative (27).

The 7-di-tert-butylaspartate derivative of 2-vinyl phylloerythrin (34) (108 mg), $CH_2Cl_2$ (50 ml), chlorotrimethylsilane (0.5 ml), and ethyleneglycol (0.5 ml) were stirred under nitrogen for 2 hours. The regular work up as described above followed by direct recrystallization from $CH_2Cl_2$/MeOH gave the 9-glycolkeutal-2-vinylphylloerythrin 7-di-tert-butylaspartate derivative (27) ketal (27) (82 mg, 72%) as a red dust.

Mp: >300° C.

λ Max nm (e): 400 (165,000), 500 (20,000), 550 (6,500), 598 (9,300), 652 (49,500).

1H NMR: 9.95, 9.90, 9.75 (each s, 3×1H, a, b and d Meso H), 8.17 (dd, 1H, 2a-CH, J=18,12), 6.62 (d, 1H, ASP N-H), 6.26 (d, 1H, 2b-CH trans to 2a-CH, J=18), 6.07 (d, 1H, 2b-CH cis to 2a-CH, J=12), 5.75 (s, 2H, 10-$CH_2$), 4.90 (X of ABX, 1H, Asp-CH), 4.70–4.55 (m, 4H, 10-glycol-$CH_2CH_2$), 4.28 (t, 2H, 7a-$CH_2$), 4.05 (q, 2H, 4a-$CH_2$), 3.68, 3.54, 3.51, 3.49, (each s, 4×3H, 1-Me, 3-Me, 5-Me, and 8-Me), 3.1 (t, 2H, 7b-$CH_2$), 2.80–2.60 (ABX, 2H, Asp-$CH_2$), 1.82 (t, 3H, 4b-Me), 1.42, 1.17 (ea s, 2×9H , both O-t-butyl), −3.20, −4.05 (each br s, 2×1H, NH).

Anal. Calcd. for $C_{47}H_{61}N_5O_7$: C 69.86 H 7.61 N 8.67. Found: C 69.74 H 7.81 N 8.65.

EXAMPLE 13

Preparation of Diels-Alder Adduct of 9-glycolketal-2-vinyl Phylloerythrin Methyl Ester (18)

This example illustrates the preparation of Diels-Alder adduct of 9-glycolketal-2-vinyl phylloerythrin methyl ester (18).

9-Glycoalkyl-2-vinyl phylloerythrin methyl ester (11) (100 mg), DMAD (1.0 ml) were dissolved in toluene (50 ml) and the reaction mixture was refluxed for 5 days. The reaction was monitored by visible spectroscopy. It was then purified by following the method discussed for Diels Alder (14). After crystallization from $CH_2Cl_2$/hexane, the compound 18 9-glycolketal-2-vinyl phylloerythrin methyl ester (18) was isolated in 52% yield.

Mp: 254°–256° C.

λ Max nm (e): 408 (200,690), 514 (17,188), 542 (14,909), 592 (11,412), 646 (36,062)1H NMR: 9.57 (s, 1H, b Meso H), 9.17, 8.94 (each s, 2×1H, a and d Meso H), 7.38 (t, 1H, 2a-CH) 5.50 (s, 2H, 10-$CH_2$), 4.6–4.5 (m, 4H,10-O—$CH_2CH_2$—O), 4.25 (t, 2H, 7a-$CH_2$) 3.85 (q, 2H, 4a-$CH_2$), 3.65 (m, 2b-$CH_2$), 3.98, 3.88, 3.76, 3.52, 3.45, 3.42 (each s, 6×3H, 1a-OMe, 1b-OMe, 3-Me, 5-Me, 7-OMe and 8-Me), 3.02 (t, 2H, 7b-$CH_2$), 2.15 (s, 3H, 1-Me), 1.74 (t, 3H, 4b-Me), −1.38, −2.25 (each br s, 2×1H, NH). MS (EI): High Resolution Calcd. for $C_{42}H_{44}N_4O_8$: 732.315915. Found: 732.317451. Low Resolution (EI): 732.3 (11.8%), 716.3 (15.0%), 688.3 (11.7), 673.3 (45.3%), 672.3 (100%).

EXAMPLE 14

Preparation of Benzoporphyrin Derivative (cis isomer) (22)

This example illustrates preparation of benzoporphyrin derivative (cis isomer) (22).

The foregoing Diels Alder adduct (18) was dissolved in dichloromethane (10 ml) and DBU (5 drops) were added. The reaction mixture was stirred at room temperature for 10 minutes under nitrogen atmosphere. The reaction mixture was purified as described for compound (15), and the desired product (22) was isolated in quantitative yield.

Mp: >300° C.

λ Max nm (e): 358 (48,860), 444 (102,300), 514 (17,440), 584 (26,140), 614 (20,791), 674 (37,932).

1H NMR: 9.60 (s, 1H, b Meso H), 9.35, 8.90 (each s, 2×1H, a and d Meso H), 7.85, 7.38 (s, 2×1H, 2a-CH and 2b-CH) 5.50 (s, 2H, 10-$CH_2$), 4.6–4.5 (m, 4H, 10-O—$CH_2CH_2$—O), 4.45 (t, 2H, 7a-$CH_2$) 3.85 (q, 2H, 4a-$CH_2$), 3.98, 3.98, 3.60, 3.50, 3.45, 3.00 (each s, 6×3H, 1a-OMe, 1b-OMe, 3-Me, 5-Me, 7-OMe and 8-Me), 3.20 (t, 2H, 7b-$CH_2$), 1.85 (s, 3H, 1-Me), 1.64 (t, 3H, 4b-Me), −1.25, −2.10 (each br s, 2×1H, NH).

EXAMPLE 15

Preparation of Diels-Alder Adduct of 2-Vinylphylloerythrin Methyl Ester (cis isomer) (24).

This example illustrates preparation of Diels-Alder adduct of 2-vinylphylloerythrin methyl ester (cis isomer) (24).

The Diels-Alder DBU rearranged product (22) (7 mg) was mixed into acetone and 1M HCl was added. The mixture was stirred for 5 minutes. The organic layer was washed, dried, and recrystallized from MeOH/$CH_2Cl_2$ to give the Diels-Alder adduct of 2-vinylphylloerythrin methyl ester (cis isomer) (24) compound (3 mg) as dark blue-black crystals.

λ Max nm (e): 442 (120,385), 616 (41,409), 664 (26,917), 668 (26,917), 1H NMR (ppm, in $CDCl_3$): 9.62, 9.30, 8.90 (each s, 1H, 3 Meso H); 7.82 and 7.42 (each d, 1H, exocyclic ring CH); 5.50 (s, 2H, 10$CH_2$); 5.02 (s, 1H, exocyclic ring $CHCO_2CH_3$); 4.45 (t, 2H, $CH_2CH_2CO_2$); 3.98, 3.97, 3.58, 3.52, 3.50 and 2.98 (each s, 3H, 3 $CH_3$ and 3 —$OCH_3$); 3.20 (t, 2H, $CH_2CH_2CO_2$); 3.98, 3.97, 3.58, 3.52, 3.50 and 2.98 (each s, 3H, 3 $CH_3$ and 3-$OCH_3$); 3.20 (t, 2H, $CH_2CH_2CO_2$); 2.38 (s, 1H, 1-$CH_3$); 1.78 (t, 3H, $CH_2CH_3$); −1.45 and 2.38 (each br S, 1H, 2NH).

MP >300° C.

EXAMPLE 16

Preparation of Diels-Alder Adduct of 9-Thiolketal of 2-Vinylphylloerythrin Methyl Ester (19)

This example illustrates preparation of Diels-Alder adduct of 9-thiolketal of 2-vinylphylloerythrin methyl ester (19).

Phylloerythrin (12) (100 mg) was reacted with DMAD by following the procedure as discussed for compound (18) and the Diels Alder adduct (19) was isolated in 50% yield.

Mp: 224°–225° C.

λ Max nm (e): 410 (245,421), 508 (25,107), 542 (22,325), 594 (17,980), 646 (43,086).

1H NMR: 9.57 (s, 1H, b Meso H), 9.28, 8.96 (each s, 2×1H, a and d Meso H), 7.35 (t, 1H, 2a-CH) 6.00 (s, 2H, 10-$CH_2$), 4.37 (t, 2H, 7a-$CH_2$) 4.0–3.9 (m, 6H, 2b-$CH_2$ and 10-ethylene thioketal-$CH_2CH_2$), 3.75 (q, 2H, 4a-$CH_2$), 3.98, 3.88, 3.76, 3.52, 3.45, 3.42 (each s, 6×3H, 1a-OMe, 1b-OMe, 3-Me, 5-Me, 7-OMe and 8-Me), 3.10 (t, 2H, 7b-$CH_2$), 2.15 (s, 3H, 1-Me), 1.74 (t, 3H, 4b-Me), −1.41, −2.31 (each br s, 2×1H, NH).

MS (EI ): High Resolution Calcd. for $C_{42}H_{44}N_4O_6S_2$: 764.270229. Found: 764.268164. Low Resolution (EI): 764.3 (33.5%), 704.3 (35.5%), 688.2 (100%)

EXAMPLE 17

Preparation of Benzoporphyrin Derivative (trans isomer) (21)

This example illustrates preparation of benzoporphyrin derivative (trans isomer) (21).

Diels Alder adduct (19) (20 mg) was treated with triethylamine (1.0 ml) for overnight, and the desired photosensitizer was isolated as discussed for benzoporphyrin derivative (16) and benzoporphyrin derivative (trans isomer) (21) was obtained in quantitative yield.

Mp: 256°–259° C.

λ Max nm (e): 356 (43,233), 438 (112,200), 512 (16,134), 574 (24,600), 608 (16,734), 664 (32,350), 668 (31,960).

1H NMR: 9.61 (s, 1H, b Meso H), 9.23, 9.15 (each s, 2×1H, a and d Meso H), 7.73, 7.35 (each d, 2×1H, 2a-CH and 2b-CH) 6.00 (s, 2H, 10-$CH_2$), 4.78 (s, 1H, 1a-CH), 4.37 (t, 2H, 7a-$CH_2$) 4.0–3.9 (m, 4H, 10-ethylene thioketal-$CH_2CH_2$), 4.23 (q, 2H, 4a-$CH_2$), 4.24, 3.95, 3.77, 3.52, 3.50, 3.45 (each s, 6×3H, 1a-OMe, 1b-OMe, 3-Me, 5-Me, 7-OMe and 8-Me), 3.10 (t, 2H, 7b-$CH_2$), 2.15 (s, 3H, 1-Me), 1.74 (t, 3H, 4b-Me), −1.53, −2.40 (each br s, 2×1H, NH).

EXAMPLE 18

Preparation of Benzoporphyrin Derivative (cis isomer) (23)

This example illustrates preparation of benzoporphyrin derivative (cis isomer) (23).

Diels Alder adduct (19) (18 mg) was treated with DBU (8 drops) similarly to other cis BPDs and the rearranged photosensitizer benzoporphyrin derivative (cis isomer) (23) was obtained in modest yield (16 mg).

Mp: 266°–268° C.

λ Max nm (e): 359 (46,920), 444 (92,420), 514 (12,880), 584 (21,896), 616 (15,548), 674 (35,270)

1H NMR: (ppm, in $CDCl_3$): 9.60, 9.28, 8.90 (each s, 1H, 3 MesoH); 7.80 and 7.42 (each d, 1H, 2 exocyclic ring CH); 6.00 (s, 2H, 10-$CH_2$); 5.02 (s, 1H, exocyclic ring $CHCO_2CH_3$); 4.20 (t, 2H, $CH_2CH_2CO_2$); 3.95 (m, 6H, 2 CHCH and —S—$CH_2CH_2$—S); 3.98, 3.78, 3.52, 3.46, 3.44, 2.98 (each s, 3H, 3 X $CH_3$ and 3X O—$CH_3$); 3.20 (t, 2H, $CH_2CH_2CO_2$); 2.15 (s, 3H, 1-$CH_3$); 1.78 (t, 3H, $CH_2CH_3$); −1.35 and −2.20 (each s, 1H, 2NH).

EXAMPLE 19

Preparation of Benzoporphyrin Derivative (cis isomer) (31)

This example illustrates preparation of benzoporphyrin derivative (cis isomer) (31).

Phylloerythrin di-tert butyl ester (34) (60 mg) in toluene (30 ml) was reacted with DMAD (0.5 ml) by following the standard methodology as discussed for other Diels Alder adducts. The intermediate was purified, but not characterized and was immediately treated with DBU. The title compound was purified by column chromatography (alumins grade III)., eluting with dichloromethane. After evaporating the solvent the product benzoporphyrin derivative (cis isomer) (31) was crystallized from dichloromethane/hexane. Yield 25 mg.

Mp 250°–52° C.

1H NMR (ppm, in $CDCl_3$): 9.52, 9.45, 8.89 (each s, 3 Meso H); 7.85 7.40 (each d, 1H, exocyclic ring CH); 6.60 (d, 1H, Asp. N NH); 5.45 (s, 2H, 10-$CH_2$); 5.05 (s, 1H, exocyclic ring $CHCO_2CH_3$); 4.52 [m, 1H, $CHCO^2CH_3$ (aspartic)]; 4.50 (m, 2H, $CH_2CH_2CO_2$); 4.15 (q, 2H, $CH_2CH_3$); 3.98, 3.50, 3.40, 3.38, 3.00 (each s, 3H, 3 $XCH_3$ and 2$XOCH_3$); 3.36–3.38 (m, 10-o—$CH_2CH_2$—O); 3.20 (m, 2H, $CH_2CH_2CO_2$); 1.42, 1.17 (each s, 9H, 2 tert Butyl); −1.28 and −2.28 (each s, 1H, 2NH).

EXAMPLE 20

Preparation of Diels-Alder Adduct of 9-Glycolketal-2-Vinylphylloerythrin Methyl Ester (18)

This example illustrates the preparation of Diels-Alder adduct of 9-glycolketal-2-vinylphylloerythrin methyl ester (18).

9-Glycoketal-2-vinylphylloerythrin methyl ester (11) (100 mg), and DMAD (1.0 ml) were dissolved in toluene (50 ml) and the reaction mixture was refluxed for 5 days. The reaction was monitored by visible spectroscopy. It was then purified by following the method discussed for Diels Alder adduct (14). After crystallization ($CH_2Cl_2$/hexane) the Diels-Alder adduct of 9-glycolketal-2-vinylphylloerythrin methyl ester (18) was isolated in 52% yield.

Mp: 254°–256° C.

λ Max nm (e): 408 (200,690), 514 (17,188), 542 (14,909), 592 (11,412), 646 (36,062).

1H NMR: 9.57 (s, 1H, b Meso H), 9.17, 8.94 (each s, 2×1H, a and d Meso H), 7.38 (t, 1H, 2a-CH) 5.50 (s, 2H, 10-$CH_2$), 4.6–4.5 (m, 4H,10-O—$CH_2CH_2$—O), 4.25 (t, 2H, 7a-$CH_2$) 3.85 (q, 2H, 4a-$CH_2$), 3.65 (m, 2b-$CH_2$), 3.98, 3.88, 3.76, 3.52, 3.45, 3.42 (each s, 6×3H, 1a-OMe, 1b-OMe, 3-Me, 5-Me, 7-OMe and 8-Me), 3.02 (t, 2H, 7b-$CH_2$), 2.15 (s, 3H, 1-Me), 1.74 (t, 3H, 4b-Me), −1.38, −2.25 (each br s, 2×1H, NH).

MS (EI): High Resolution Calcd. for $C_{42}H_{44}N_4O_8$: 732.315915. Found: 732.317451. Low Resolution (EI): 732.3 (11.8%), 716.3 (15.0%), 688.3 (11.7), 673.3 (45.3%), 672.3 (100%).

EXAMPLE 21

Evaluation of Rhodoporphyrin Photosensitizers

This example illustrates evaluation of rhodoporphyrin photosensitizers for their biological activity.

The new photosensitizers were screened in a mouse/tumor model system, and efficacy was related to data previously established for benzoporphyrin derivative (QLT drug) at Roswell Park Cancer Institute. A model system consisted observing the size reduction of the SMT-F tumor, a fast growing spontaneous mouse mammary tumor subline, transplanted subcutaneously to male or female DBA/2 HA-DD mice according to method described in *Adv. Med. Biol.*, 166: 3–13 (1983). The tumor line was maintained in vivo via serial transplantation in the same mouse strain. DBA/2 HA-DD mice are readily available and were obtained locally.

When mice were both the appropriate age (approximately 6 weeks) and weight (approximately 20 g), small pieces of tumor (1–2 mm cube) were transplanted with a 18 gauge trocar from a donor tumor to recipient mouse. This technique provides for relatively uniform tumor size and allows location of the tumor in the right axillary region of the animal within each experimental group. Only animals with single tumors were chosen for experiments. When tumors reached 3–4 diameter, the animal were injected with the potential photosensitizer chosen from the group described above. Prior to irradiation, the fur over grown and surrounding the tumor was removed with electric clippers. Twenty-four hours after injecting the drug, the mouse was placed in a custom-made aluminum holder. The drug and light dose required to yield a standard tumor response has already been established for BPD prior to the testing and the same treatment conditions were used for the initial screening of the new materials.

Drug Dose

Standard drug dose was 1.0 mg/kg administered by i.p. injection at 24 hours and 3 hours prior to photoillumination. BPD was used at 5.0 and 1.0 mg/kg at 24 and 3 hours post injection of the drug. See Table 1.

Irradiation Conditions

Standard light dose was 75 mW/cm$^2$ for 30 minutes for a total incident light dose of 135 J/cm$^2$ from a tunable dye laser tuned to the maximum red absorption peak. Spectra Physics 2040, a quartz fiber fitted with a microlens, was interfaced to the dye laser to deliver a uniform field of light. Laser output was measured with a power meter. Treatment areas included a minimum of 1 mm of normal tissue adjacent to the tumor.

Tumor Response

Standard tumor response to the combination of the drug and light doses outlined above, resulted in 60% nonpalpable tumors with "light to moderate" scar formation at day 7 after photoillumination.

Experimental Procedure

Following light exposure, the mice were kept in groups of 5 per cage and supplied with pelleted food and tap water ad libitum. Tumor size and gross appearance of both tumor and overlying surrounding skin was monitored daily for 80 days after photoillumination unless growth of non-responsive tumor require early sacrifice of those animals.

Photosensitizers in powder form were used for all experiments. The powder (known amount) was dissolved in known quantity of Tween 80 (Alderich), it was then diluted ten times with saline solution. The solution was then filtered through syringe filter. The concentration of the solution was determined on the basis of the extinction coefficient value of the photosensitizer at the longest wavelength absorption. Absorption spectra were obtained using Perkin Elmer 330 spectrophotometer.

Before injecting to mice, the purity of the compounds was ascertained by analytical HPLC using Spectra Physics, connected with C8 reverse phase column, length 250 mm, internal diameter 4.00 mm, eluted with methanol/water by adjusting the pH to 7.0 using phosphate buffer.

What is claimed is:

1. A compound of the formula

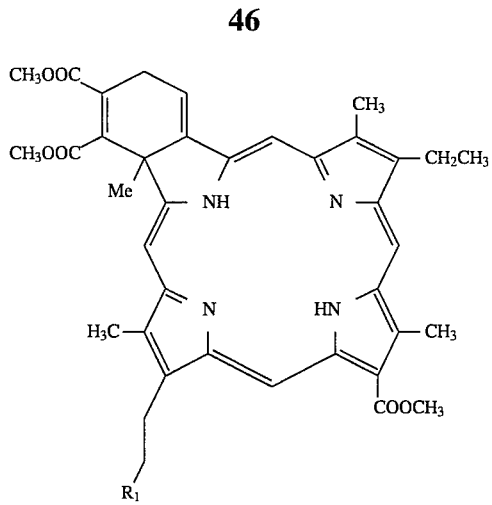

wherein $R_1$ is $COOR_2$ wherein $R_2$ is H or lower alkyl having from 1–4 carbon atoms, or —CONHCH(COOR$_3$)CH$_2$(COOR$_3$); wherein is $R_3$ is H or lower alkyl having 1–4 carbon atoms;

and the pharmaceutically acceptable salts and esters thereof.

2. A compound of the formula

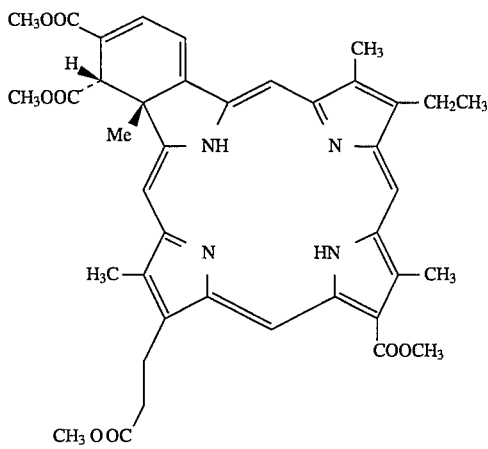

3. A compound of the formula

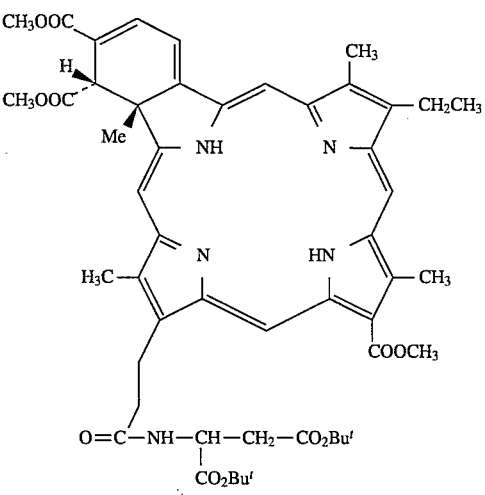

4. A compound of the formula

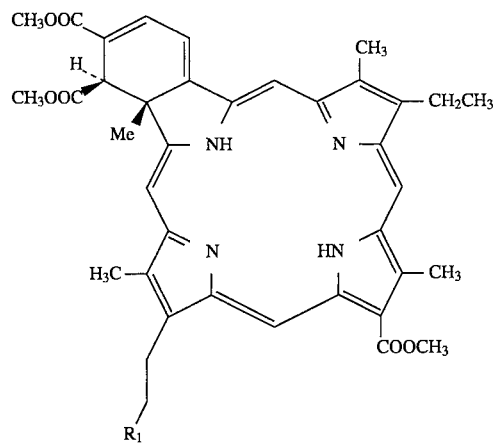

wherein $R_1$ is $COOR_2$; $R_2$ is H or lower alkyl having from 1–4 carbon atoms, or —$CONHCH(COOR_3)CH_2$ ($COOR_3$); $R_3$ is H or lower alkyl having 1–4 carbon atoms;

and the pharmaceutically acceptable salts and esters thereof.

5. A compound of the formula

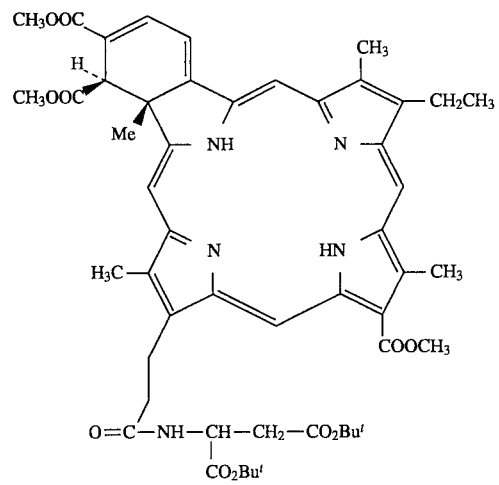

6. A compound of the formula

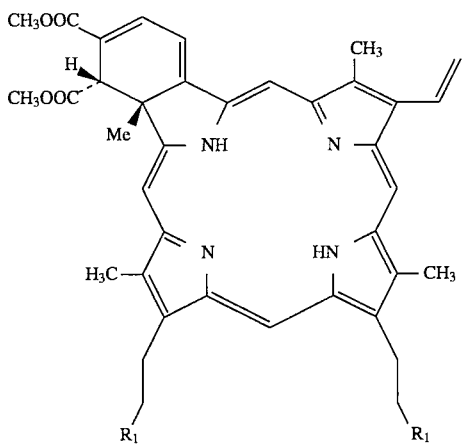

wherein $R_1$ is $COOR_2$; $R_2$ is H or lower alkyl having from 1–4 carbon atoms, or —$CONHCH(COOR_3)CH_2$ ($COOR_3$); and $R_3$ is H or lower alkyl having 1–4 carbon atoms; and the pharmaceutically acceptable salts and esters thereof;

with a proviso that $R_1$ cannot both be —$CH_2CH_2COOR_2$.

7. A method for tumor localization and treatment by photosensitization comprising steps:

(a) administering to a person in need of such treatment a photosynthesizer of claims 1 or 4;

(b) activating the compound of step (a) or appropriate salt or ester thereof with a light between 600–800 nm at an energy density between 25–100 J/cm² for 5–35 minutes.

* * * * *